United States Patent
Nemoto et al.

(10) Patent No.: US 11,429,024 B2
(45) Date of Patent: Aug. 30, 2022

(54) RADIATION-SENSITIVE RESIN COMPOSITION, RESIST PATTERN-FORMING METHOD, COMPOUND, AND METHOD OF CONTROLLING ACID DIFFUSION

(71) Applicant: JSR CORPORATION, Tokyo (JP)

(72) Inventors: Ryuichi Nemoto, Tokyo (JP); Tsuyoshi Furukawa, Tokyo (JP)

(73) Assignee: JSR CORPORATION, Tokyo (JP)

( * ) Notice: Subject to any disclaimer, the term of this patent is extended or adjusted under 35 U.S.C. 154(b) by 334 days.

(21) Appl. No.: 16/893,460

(22) Filed: Jun. 5, 2020

(65) Prior Publication Data
US 2020/0393755 A1    Dec. 17, 2020

(30) Foreign Application Priority Data
Jun. 17, 2019 (JP) .............................. JP2019-112329

(51) Int. Cl.
| | | |
|---|---|---|
| G03F 7/004 | (2006.01) | |
| C07C 69/712 | (2006.01) | |
| G03F 7/038 | (2006.01) | |
| G03F 7/039 | (2006.01) | |
| C08F 220/28 | (2006.01) | |
| C08F 220/38 | (2006.01) | |
| C08F 220/18 | (2006.01) | |
| C07D 327/04 | (2006.01) | |
| C07D 309/12 | (2006.01) | |
| C07D 319/20 | (2006.01) | |
| C07C 65/21 | (2006.01) | |
| C07C 323/12 | (2006.01) | |

(Continued)

(52) U.S. Cl.
CPC ............ *G03F 7/0045* (2013.01); *C07C 25/02* (2013.01); *C07C 65/21* (2013.01); *C07C 69/712* (2013.01); *C07C 323/12* (2013.01); *C07C 381/12* (2013.01); *C07D 309/12* (2013.01); *C07D 319/20* (2013.01); *C07D 327/04* (2013.01); *C08F 220/1805* (2020.02); *C08F 220/283* (2020.02); *C08F 220/382* (2020.02); *C08F 220/387* (2020.02); *G03F 7/038* (2013.01); *G03F 7/039* (2013.01); *C07C 2601/08* (2017.05); *C07C 2601/14* (2017.05); *C07C 2603/74* (2017.05); *G03F 7/162* (2013.01); *G03F 7/168* (2013.01); *G03F 7/2006* (2013.01); *G03F 7/325* (2013.01); *G03F 7/38* (2013.01)

(58) Field of Classification Search
None
See application file for complete search history.

(56) References Cited

U.S. PATENT DOCUMENTS

| | | |
|---|---|---|
| 4,822,718 A | 4/1989 | Latham et al. |
| 4,876,165 A | 10/1989 | Brewer et al. |
| 4,910,122 A | 3/1990 | Arnold et al. |
| 5,674,648 A | 10/1997 | Brewer et al. |

(Continued)

FOREIGN PATENT DOCUMENTS

| | | |
|---|---|---|
| JP | 5993448 A | 5/1984 |
| JP | 6-012452 B2 | 2/1994 |
| JP | 2009014815 A | 1/2009 |
| JP | 2009134088 A | 6/2009 |

(Continued)

OTHER PUBLICATIONS

Machine translation of WO 2012/063840, published on May 18, 2012 (Year: 2012).*

(Continued)

*Primary Examiner* — Anca Eoff
(74) *Attorney, Agent, or Firm* — Element IP, PLC

(57) ABSTRACT

The radiation-sensitive resin composition contains: a polymer having a structural unit that includes an acid-labile group; and a compound represented by formula (1). In the formula (1), $Ar^1$ represents a group obtained by removing (m+n+2) hydrogen atoms from an aromatic ring of an arene having 6 to 30 carbon atoms; —OH and —COO— are bonded at ortho positions to each other on a same benzene ring on $Ar^1$; and $R^G$ represents a group represented by formula (V-1), a group represented by formula (V-2), a group including a lactone structure, a group including a cyclic carbonate structure, a group including a sultone structure, a group including a ketonic carbonyl group, a group including a thiocarbonate group, or a group including a group represented by formula (V-3), or the like.

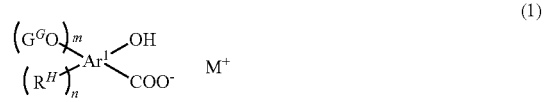

(1)

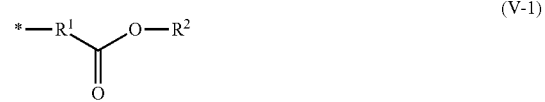

(V-1)

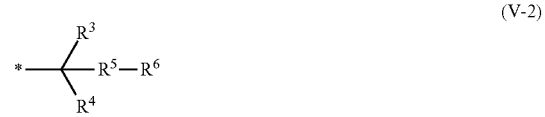

(V-2)

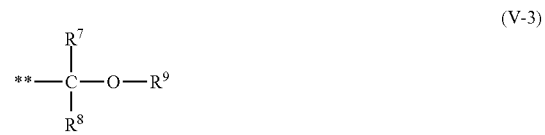

(V-3)

10 Claims, No Drawings

(51) Int. Cl.
*C07C 25/02* (2006.01)
*C07C 381/12* (2006.01)
*G03F 7/32* (2006.01)
*G03F 7/16* (2006.01)
*G03F 7/20* (2006.01)
*G03F 7/38* (2006.01)

(56) References Cited

U.S. PATENT DOCUMENTS

2013/0189619 A1* 7/2013 Komuro ............... G03F 7/0046
430/325
2017/0097564 A1* 4/2017 Nagamine ............ G03F 7/0046

FOREIGN PATENT DOCUMENTS

JP          2013200560 A    10/2013
WO    WO 2012/063840      *  5/2015

OTHER PUBLICATIONS

Winkle, M.R., Ronald, R.C.—Regioselective Metalation Reactions of Some Substituted (Methoxymethoxy)arenes, J.Org.Chem, 1982, 47, pp. 2101-2108 (Year: 1982).*

* cited by examiner

RADIATION-SENSITIVE RESIN COMPOSITION, RESIST PATTERN-FORMING METHOD, COMPOUND, AND METHOD OF CONTROLLING ACID DIFFUSION

CROSS-REFERENCE TO RELATED APPLICATIONS

The present application claims priority to Japanese patent application No. 2019-112329, filed Jun. 17, 2019, the contents of which are incorporated herein by reference in their entirety.

BACKGROUND OF THE INVENTION

Field of the Invention

The present invention relates to a radiation-sensitive resin composition, a resist pattern-forming method, a compound, and a method of controlling acid diffusion.

Description of the Related Art

Radiation-sensitive resin compositions for use in microfabrication by lithography generate an acid at a light-exposed region upon irradiation with a radioactive ray, e.g., an electromagnetic wave such as a far ultraviolet ray such as an ArF excimer laser beam (wavelength of 193 nm), a KrF excimer laser beam (wavelength of 248 nm), etc., an extreme ultraviolet ray (EUV), or a charged particle ray such as an electron beam. A chemical reaction in which the acid serves as a catalyst causes a difference in rates of dissolution in a developer solution between light-exposed regions and light-unexposed regions, whereby a resist pattern is formed on a substrate.

Such radiation-sensitive resin compositions are required not only to have favorable sensitivity to exposure light, but also to have superiority with regard to each of LWR (Line Width Roughness) performance, which indicates line width uniformity, and CDU (Critical Dimension Uniformity) performance, which indicates variance of line widths in greater ranges. To meet such requirements, types, molecular structures, and the like of polymers, acid generating agents, and other components which may be used in radiation-sensitive resin compositions have been investigated (see Japanese Unexamined Patent Publication, Publication Nos. 2009-14815 and 2013-200560).

SUMMARY OF THE INVENTION

According to an aspect of the present invention, a compound is represented by formula (1):

(1)

In the formula (1), $Ar^1$ represents a group obtained by removing (m+n+2) hydrogen atoms from an aromatic ring of an arene having 6 to 30 carbon atoms; and —OH and —COO— are bonded at ortho positions to each other on a same benzene ring on $Ar^1$. m is an integer of 1 to 16. In a case in which m is 1, $R^G$ represents a group represented by formula (V-1), a group represented by formula (V-2), a group comprising a lactone structure, a group comprising a cyclic carbonate structure, a group comprising a sultone structure, a group comprising a ketonic carbonyl group, a group comprising a thiocarbonate group, or a group comprising a group represented by formula (V-3). In a case in which m is no less than 2, a plurality of $R^G$s are identical or different from each other, and each $R^G$ represents a group represented by the formula (V-1), a group represented by the formula (V-2), a group comprising a lactone structure, a group comprising a cyclic carbonate structure, a group comprising a sultone structure, a group comprising a ketonic carbonyl group, a group comprising a thiocarbonate group, or a group comprising a group represented by the formula (V-3), or the plurality of $R^G$s taken together represent a part of a ring structure having 5 to 20 ring atoms constituted together with the atomic chain to which the plurality of $R^G$s bond. n is an integer of 0 to 15. In a case in which n is 1, $R^H$ represents a halogen atom or a substituted or unsubstituted monovalent hydrocarbon group having 1 to 20 carbon atoms. In a case in which n is no less than 2, a plurality of $R^H$s are identical or different from each other, and each $R^H$ represents a halogen atom or a substituted or unsubstituted monovalent hydrocarbon group having 1 to 20 carbon atoms, or the plurality of $R^H$s taken together represent a part of an alicyclic structure having 4 to 20 ring atoms constituted together with the carbon chain to which the plurality of $R^H$s bond. A sum of m and n is no greater than 16; and $M^+$ is a monovalent radiation-sensitive cation.

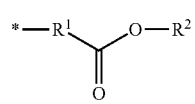

(V-1)

In the formula (V-1), $R^1$ represents a substituted or unsubstituted divalent hydrocarbon group having 1 to 20 carbon atoms; $R^2$ represents a monovalent organic group having 1 to 20 carbon atoms; and * denotes a binding site to an oxygen atom adjacent to $Ar^1$ in the formula (1),

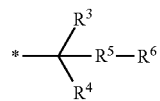

(V-2)

In the formula (V-2), $R^3$ and $R^4$ each independently represent a hydrogen atom or a substituted or unsubstituted monovalent hydrocarbon group having 1 to 20 carbon atoms; $R^5$ represents —O— or —S—; and $R^6$ represents a monovalent organic group having 1 to 20 carbon atoms, or $R^4$, $R^5$, and $R^6$ taken together represent a part of a ring structure having 4 to 20 ring atoms constituted together with the atomic chain to which $R^4$, $R^5$, and $R^6$ bond; and * denotes a binding site to an oxygen atom adjacent to $Ar^1$ in the formula (1).

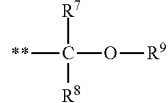

(V-3)

In the formula (V-3), $R^7$ represents a fluorine atom or a monovalent fluorinated hydrocarbon group having 1 to 20 carbon atoms; $R^8$ represents a hydrogen atom, a fluorine atom, or a monovalent organic group having 1 to 20 carbon atoms; $R^9$ represents a hydrogen atom or a monovalent organic group having 1 to 20 carbon atoms; and ** denotes a binding site to an oxygen atom adjacent to $Ar^1$ in the formula (1) or to a part other than the group represented by the formula (V-3) in $R^G$.

According to another aspect of the present invention, a radiation-sensitive resin composition includes: a polymer including a structural unit including an acid-labile group; and the above-mentioned compound.

According to further aspect of the present invention, a resist pattern-forming method includes applying a radiation-sensitive resin composition directly or indirectly on a substrate to form a resist film. The resist film is exposed. The resist film exposed is developed. The radiation-sensitive resin composition includes: a polymer including a structural unit including an acid-labile group; and the above-mentioned compound.

According to a further aspect of the present invention, a method of controlling acid diffusion includes irradiating a composition which includes the above-mentioned compound and an acid generator with a radioactive ray. The acid generator is capable of generating an acid by irradiation with the radioactive ray.

DESCRIPTION OF THE EMBODIMENTS

According to one embodiment of the invention, a radiation-sensitive resin composition contains a polymer (hereinafter, may be also referred to as "(A) polymer" or "polymer (A)") having a structural unit (hereinafter, may be also referred to as "structural unit (I)") that includes an acid-labile group; and a compound (hereinafter, may be also referred to as "(C) compound" or "compound (C)") represented by the following formula (1):

$$\begin{array}{c}(R^GO)_m \quad \diagup OH \\ \diagdown Ar^1 \diagup \quad M^+ \\ (R^H)_n \quad \diagdown COO^- \end{array} \quad (1)$$

wherein, in the above formula (1), $Ar^1$ represents a group obtained by removing (m+n+2) hydrogen atoms from an aromatic ring of an arene having 6 to 30 carbon atoms;

—OH and —COO— are bonded at ortho positions to each other on a same benzene ring on $Ar^1$;

m is an integer of 1 to 16, wherein in a case in which m is 1, $R^G$ is a group represented by formula (V-1), a group represented by formula (V-2), a group containing a lactone structure, a group containing a cyclic carbonate structure, a group containing a sultone structure, a group containing a ketonic carbonyl group, a group containing a thiocarbonate group, or a group containing a group represented by formula (V-3), and in a case in which m is no less than 2, a plurality of $R^G$s are identical or different from each other and are each a group represented by the formula (V-1), a group represented by the formula (V-2), a group containing a lactone structure, a group containing a cyclic carbonate structure, a group containing a sultone structure, a group containing a ketonic carbonyl group, a group containing a thiocarbonate group, or a group containing a group represented by formula (V-3), or the plurality of $R^G$s taken together represent a part of a ring structure having 5 to 20 ring atoms constituted together with the atomic chain to which the plurality of $R^G$s bond;

n is an integer of 0 to 15, wherein in a case in which n is 1, $R^H$ is a substituted or unsubstituted monovalent hydrocarbon group having 1 to 20 carbon atoms, or a halogen atom, and in a case in which n is no less than 2, a plurality of $R^H$s are identical or different from each other, and each represents a substituted or unsubstituted monovalent hydrocarbon group having 1 to 20 carbon atoms, or a halogen atom, or the plurality of $R^H$s taken together represent a part of an alicyclic structure having 4 to 20 ring atoms constituted together with the carbon chain to which the plurality of $R^H$s bond, and wherein a sum of m and n is no greater than 16; and $M^+$ is a monovalent radiation-sensitive cation, $$*-R^1 \underset{\underset{O}{\|}}{C} O-R^2 \qquad (V\text{-}1)$$

in the above formula (V-1), $R^1$ represents a substituted or unsubstituted divalent hydrocarbon group having 1 to 20 carbon atoms;

$R^2$ represents a monovalent organic group having 1 to 20 carbon atoms; and

* denotes a binding site to an oxygen atom adjacent to $Ar^1$ in the above formula (1), $$*-\underset{R^4}{\overset{R^3}{\underset{|}{C}}}-R^5-R^6 \qquad (V\text{-}2)$$

in the above formula (V-2), $R^3$ and $R^4$ each independently represent a substituted or unsubstituted monovalent hydrocarbon group having 1 to 20 carbon atoms, or a hydrogen atom;

$R^5$ represents —O— or —S—; and $R^6$ represents a monovalent organic group having 1 to 20 carbon atoms, or $R^4$, $R^5$, and $R^6$ taken together represent a part of a ring structure having 4 to 20 ring atoms constituted together with the atomic chain to which $R^4$, $R^5$, and $R^6$ bond; and

* denotes a binding site to an oxygen atom adjacent to $Ar^1$ in the above formula (1), and $$**-\underset{R^8}{\overset{R^7}{\underset{|}{C}}}-O-R^9 \qquad (V\text{-}3)$$

in the above formula (V-3), $R^7$ represents a fluorine atom or a monovalent fluorinated hydrocarbon group having 1 to 20 carbon atoms;

$R^8$ represents a hydrogen atom, a fluorine atom, or a monovalent organic group having 1 to 20 carbon atoms;

R[9] represents a hydrogen atom or a monovalent organic group having 1 to 20 carbon atoms; and

** denotes a binding site to an oxygen atom adjacent to Ar[1] in the above formula (1) or to a part other than the group represented by the above formula (V-3) in $R^G$.

According to another embodiment of the invention, a resist pattern-forming method includes: applying a radiation-sensitive resin composition directly or indirectly on a substrate;

exposing a resist film formed by the applying; and developing the resist film exposed, wherein the radiation-sensitive resin composition contains the polymer (A) and the compound (C).

According to a still another embodiment of the invention, an acid diffusion control agent is represented by the above formula (1).

The compound (C) is yet another embodiment of the invention.

The radiation-sensitive resin composition, the resist pattern-forming method, the acid diffusion control agent, and the compound of the embodiments of the present invention enable a resist pattern to be formed with favorable sensitivity to exposure light, and superiority with regard to each of LWR performance and CDU performance, even under current circumstances in which miniaturization of resist patterns has proceeded to a level for line widths of no greater than 40 nm. Therefore, these can be suitably used in the manufacture of semiconductor devices, in which further progress of miniaturization is expected in the future. Hereinafter, the embodiments of the present invention will be explained in detail.

Radiation-Sensitive Resin Composition

The radiation-sensitive resin composition according to an embodiment of the present invention contains the polymer (A) and the compound (C). The radiation-sensitive resin composition may contain, as favorable components: an acid generator (B); an acid diffusion controller (hereinafter, may be also referred to as "acid diffusion controller (c)") other than the compound (C); a solvent (D); and a second polymer (hereinafter, may be also referred to as "(E) polymer" or "polymer (E)") in which a total percentage content by mass of fluorine atoms is greater than that in the polymer (A), and may also contain other optional component(s) within a range not leading to impairment of the effects of the present invention.

Due to the polymer (A) and the compound (C) being contained, the radiation-sensitive resin composition enables a resist pattern to be formed with favorable sensitivity to exposure light and superiority with regard to each of LWR performance and CDU performance. Although not necessarily clarified and without wishing to be bound by any theory, the reason for achieving the aforementioned effects by the radiation-sensitive resin composition due to involving such a constitution may be presumed, for example, as in the following. Owing to the sterically bulky structure of the compound (C) contained in the radiation-sensitive resin composition, it is considered that a diffusion length of an acid generated by exposing the resist film shortens, thereby improving both LWR performance and CDU performance. It is to be noted that in the case in which the radiation-sensitive resin composition contains the acid generator (B), it is considered that a diffusion length of an acid generated from the acid generator (B) is shortened at light-exposed regions of the resist film and that the compound (C) functions as a base acting on the acid in the light-unexposed regions, thereby improving both the LWR performance and the CDU performance of the radiation-sensitive resin composition as a result. Each component of the radiation-sensitive resin composition will be described below.

(A) Polymer

The polymer (A) has the structural unit (hereinafter, may be also referred to as "structural unit (I)") that includes the acid-labile group. In addition to the structural unit (I), the polymer (A) preferably has: a structural unit (hereinafter, may be also referred to as "structural unit (II)") containing a lactone structure, a cyclic carbonate structure, a sultone structure, or a combination thereof; a structural unit (hereinafter, may be also referred to as "structural unit (III)") that includes an alcoholic hydroxyl group; and/or a structural unit (hereinafter, may be also referred to as "structural unit (IV)") that includes a phenolic hydroxyl group, and may include other structural unit(s) than the structural units (I) to (IV). The polymer (A) may have one, or two or more types of each structural unit. Each structural unit will be described below.

Structural Unit (I)

The structural unit (I) includes the acid-labile group. The "acid-labile group" as referred to herein means a group that substitutes for a hydrogen atom of a carboxy group or a phenolic hydroxyl group, and is dissociable by an action of an acid. The "ring structure" is exemplified by an alicyclic structure and an aromatic ring structure. When the polymer (A) includes the acid-labile group in the structural unit (I), the acid-labile group is dissociated in the light-exposed regions by an action of the acid generated by the exposing, and a difference in solubility in a developer solution emerges between the light-exposed regions and the light-unexposed regions, thereby enabling forming the resist pattern.

The structural unit (I) is exemplified by a structural unit (hereinafter, may be also referred to as "structural unit (I-1A), (I-1B), (I-2A), and (1-2B)") represented by the following formula (2-1A), formula (2-1B), formula (2-2A), and formula (2-2B), respectively, and the like. It is to be noted that in each of the structural units (I-1A) to (I-2B), $-CR^XR^YR^Z$ or $-CR^UR^V(OR^W)$ bonding to an oxy-oxygen atom derived from the carboxy group or the phenolic hydroxyl group corresponds to the acid-labile group.

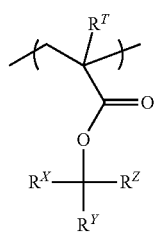

(2-1A)

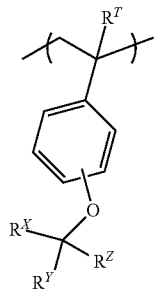

(2-1B)

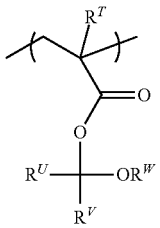

(2-2A)

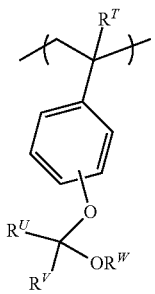

(2-2B)

In each of the above formulae (2-1A) and (2-1B), $R^T$ represents a hydrogen atom, a fluorine atom, a methyl group, or a trifluoromethyl group; $R^X$ represents a monovalent hydrocarbon group having 1 to 20 carbon atoms; $R^Y$ and $R^Z$ each independently represent a monovalent hydrocarbon group having 1 to 20 carbon atoms, or $R^Y$ and $R^Z$ taken together represent a part of an alicyclic structure having 3 to 20 ring atoms or an aliphatic heterocyclic ring structure having 5 to 20 ring atoms, the alicyclic structure or the aliphatic heterocyclic structure being constituted together with the carbon atom to which $R^Y$ and $R^Z$ bond.

In each of the above formulae (2-2A) and (2-2B), $R^T$ represents a hydrogen atom, a fluorine atom, a methyl group, or a trifluoromethyl group; $R^U$ represents a hydrogen atom or a monovalent hydrocarbon group having 1 to 20 carbon atoms; $R^V$ and $R^W$ each independently represent a monovalent hydrocarbon group having 1 to 20 carbon atoms, or $R^V$ and $R^W$ taken together represent a part of an aliphatic heterocyclic structure having 4 to 20 ring atoms constituted together with the carbon atom to which $R^U$ bonds and the oxygen atom adjacent to the carbon atom.

The monovalent hydrocarbon group containing 1 to 20 carbon atoms which may be represented by $R^X$, $R^Y$, $R^Z$, $R^U$, $R^V$, or $R^W$ is exemplified by a monovalent chain hydrocarbon group having 1 to 20 carbon atoms, a monovalent alicyclic hydrocarbon group having 3 to 20 carbon atoms, a monovalent aromatic hydrocarbon group having 6 to 20 carbon atoms, and the like.

Examples of the monovalent chain hydrocarbon group having 1 to 20 carbon atoms include: alkyl groups such as a methyl group, an ethyl group, an n-propyl group, and an i-propyl group; alkenyl groups such as an ethenyl group and a propenyl group; alkynyl groups such as an ethynyl group and a propynyl group; and the like. Examples of the monovalent alicyclic hydrocarbon group having 3 to 20 carbon atoms include: alicyclic saturated hydrocarbon groups such as a cyclopentyl group, a cyclohexyl group, a norbornyl group, and an adamantyl group; alicyclic unsaturated hydrocarbon groups such as a cyclopentenyl group, a cyclohexenyl group, and a nobornenyl group; and the like. Examples of the monovalent aromatic hydrocarbon group having 6 to 20 carbon atoms include: aryl groups such as a phenyl group, a tolyl group, a xylyl group, a naphthyl group, and an anthryl group; aralkyl groups such as a benzyl group, a phenethyl group, a napthylmethyl group, and an anthrylmethyl group; and the like.

Examples of the alicyclic structure having 3 to 20 ring atoms which may be represented by $R^Y$ and $R^Z$ taken together include: saturated alicyclic structures such as a cyclopropane structure, a cyclobutane structure, a cyclopentane structure, a cyclohexane structure, a norbornane structure, and an adamantane structure; unsaturated alicyclic structures such as a cyclopropene structure, a cyclobutene structure, a cyclopentene structure, a cyclohexene structure, and a norbornene structure; and the like.

Examples of the aliphatic heterocyclic structure having 4 to 20 ring atoms which may be represented by $R^V$ and $R^W$ taken together include: saturated oxygen-containing heterocyclic structures such as an oxacyclobutane structure, an oxacyclopentane structure, and an oxacyclohexane structure; unsaturated oxygen-containing heterocyclic structures such as an oxacyclobutene structure, an oxacyclopentene structure, and an oxacyclohexene structure; and the like.

In light of a degree of copolymerization of a monomer that gives the structural unit (I), $R^T$ represents preferably a hydrogen atom or a methyl group. $R^X$ represents preferably a hydrogen atom, the alkyl group, or the alyl group. $R^Y$ and $R^Z$ each represent preferably the alkyl group or the alicyclic saturated hydrocarbon group. The structural unit (I) is preferably the structural unit (I-1A).

The lower limit of a proportion of the structural unit (I) contained with respect to total structural units constituting the polymer (A) is preferably 15 mol %, more preferably 25 mol %, and still more preferably 30 mol %. The upper limit of the proportion is preferably 75 mol %, more preferably 65 mol %, and particularly preferably 60 mol %. When the proportion falls within the above range, the sensitivity of the radiation-sensitive resin composition to exposure light can be further increased, and as a result, the LWR performance and the CDU performance can be further improved.

Structural Unit (II)

The structural unit (II) contains a lactone structure, a cyclic carbonate structure, a sultone structure, or a combination thereof. When the polymer (A) has the structural unit (II), solubility in the developer solution of the polymer (A) can be more appropriately adjusted, and as a result, the LWR performance and the CDU performance of the radiation-sensitive resin composition can be further improved. The structural unit (II) is exemplified by structural units represented by the following formulae, and the like.

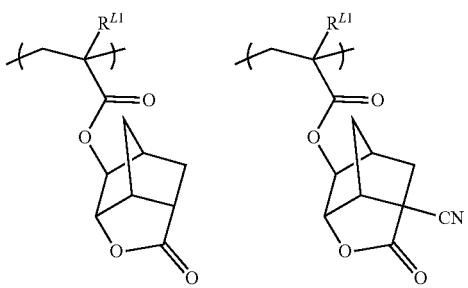

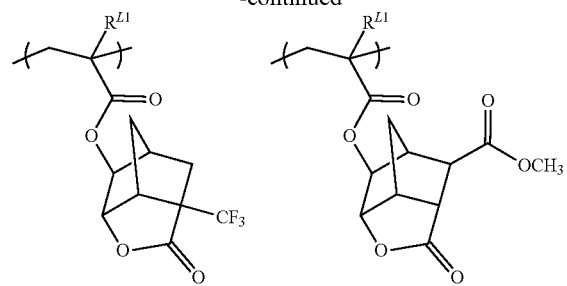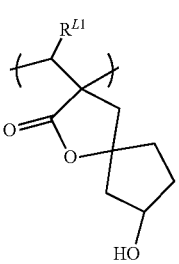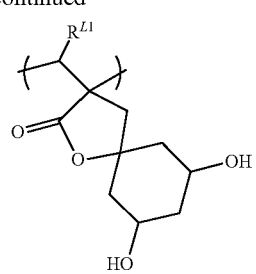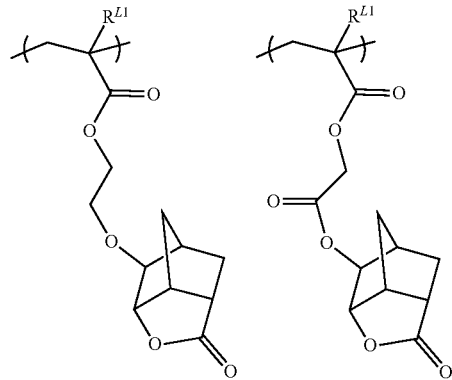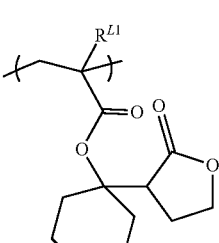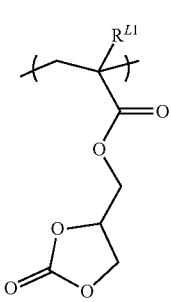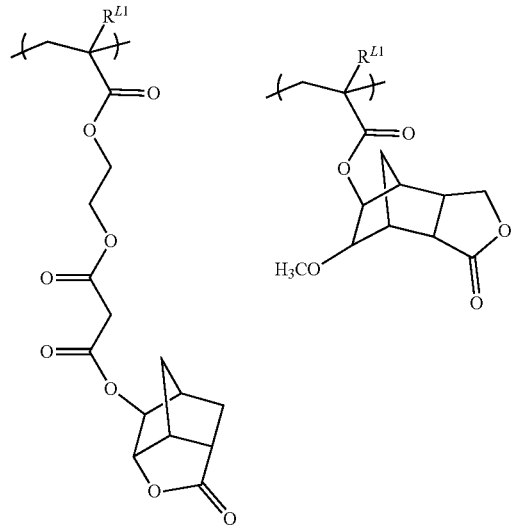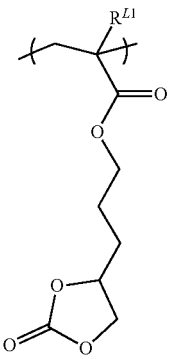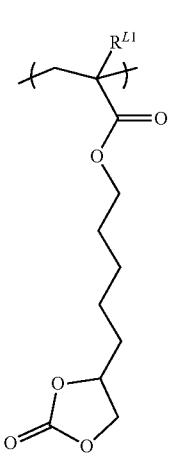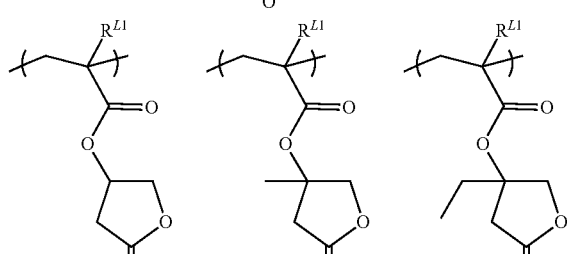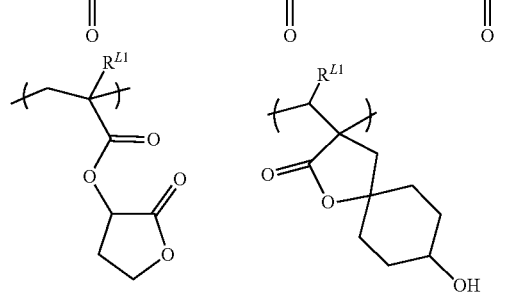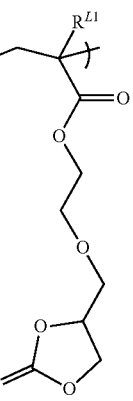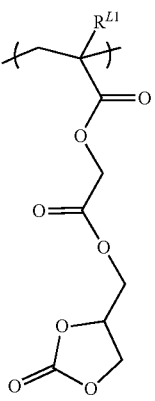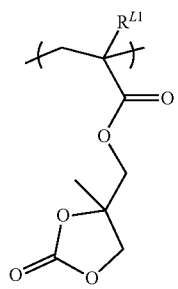

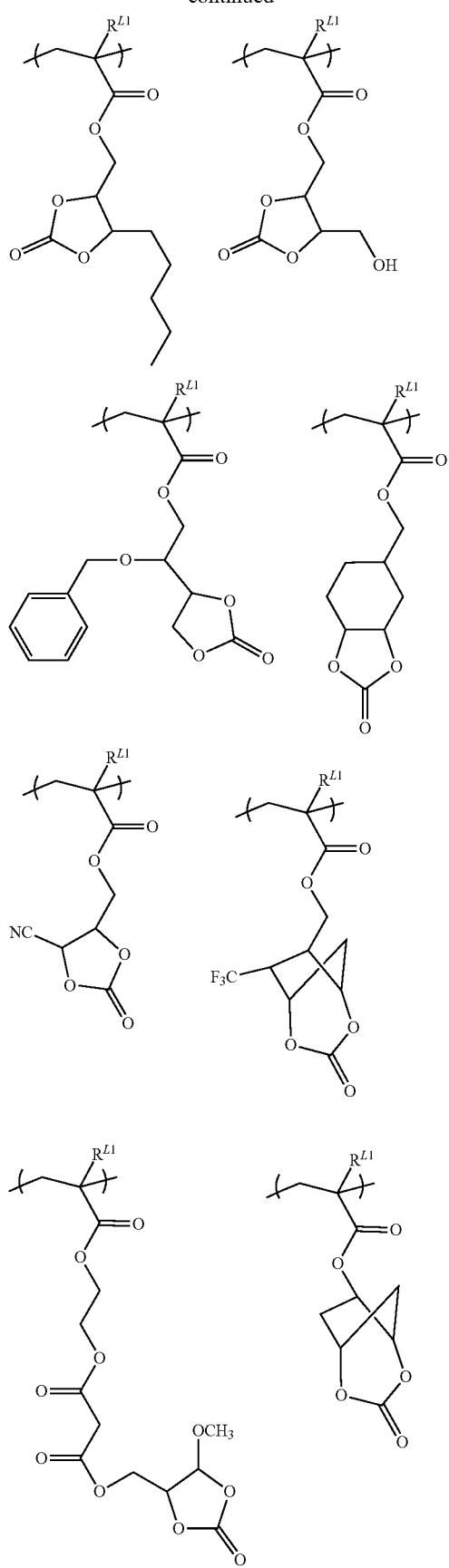
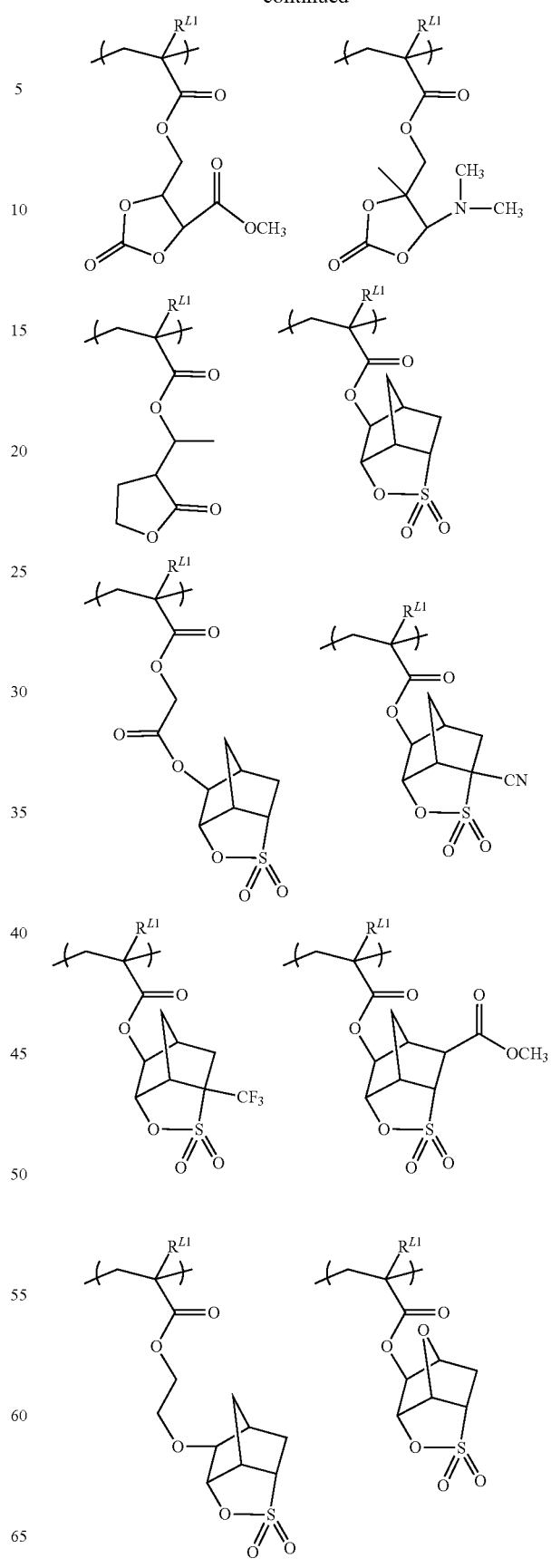

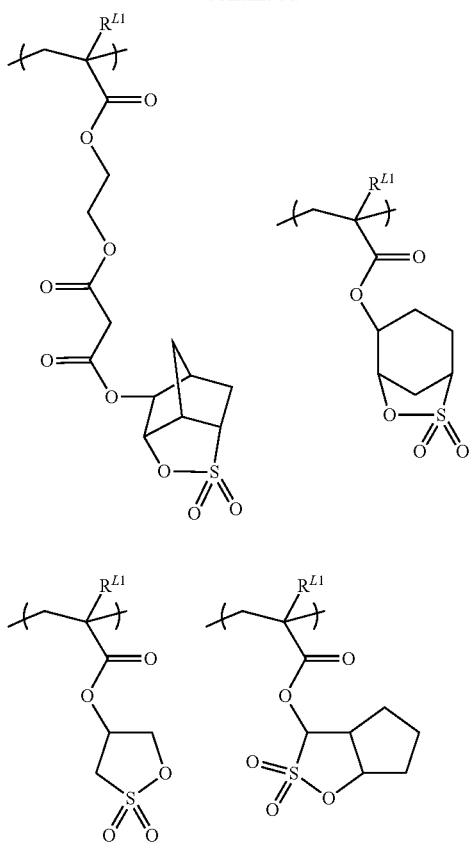

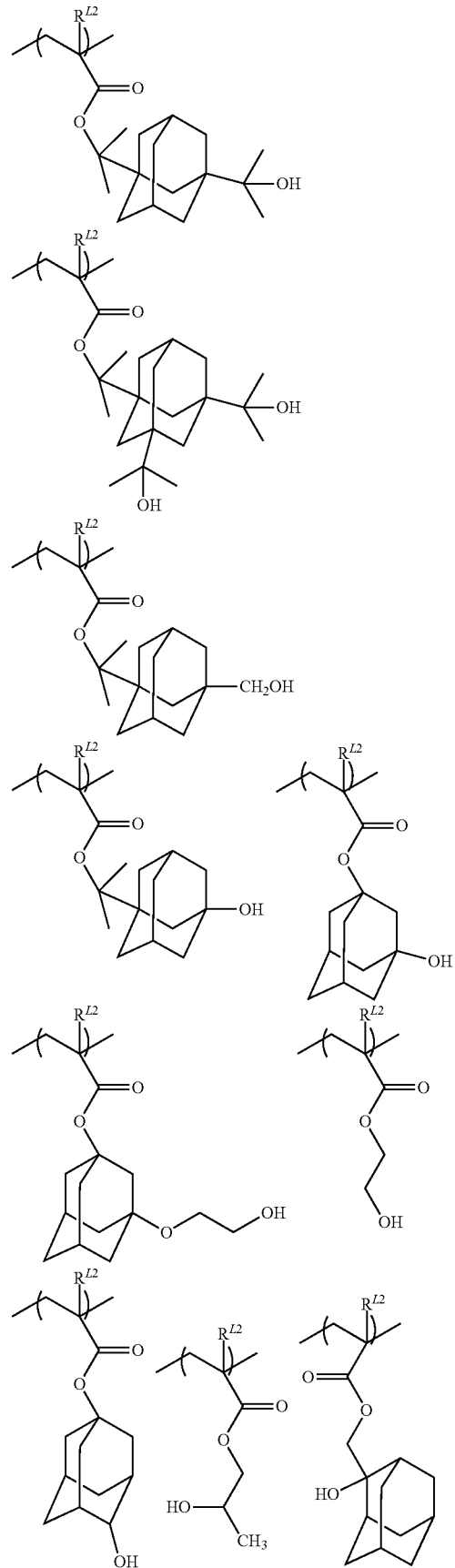

In each of the above formulae, $R^{L1}$ represents a hydrogen atom, a fluorine atom, a methyl group, or a trifluoromethyl group. The structural unit (II) preferably contains the lactone structure or the sultone structure.

The lower limit of a proportion of the structural unit (II) contained with respect to total structural units in the polymer (A) is preferably 10 mol %, more preferably 20 mol %, and still more preferably 25 mol %. The upper limit of the proportion is preferably 80 mol %, more preferably 70 mol %, and still more preferably 65 mol %. Such a proportion is particularly preferable in a case in which the exposure light is an ArF excimer laser beam. In a case in which the exposure light is EUV, the lower limit of the proportion with respect to the total structural units is preferably 1 mol %, and more preferably 5 mol %. The upper limit of the proportion is preferably 35 mol %, and more preferably 25 mol %. When the proportion of the structural unit (II) falls within the above range, solubility in the developer solution of the polymer (A) can be more appropriately adjusted, and as a result, the LWR performance and the CDU performance can be further improved.

Structural Unit (III)

The structural unit (III) contains an alcoholic hydroxyl group. When the polymer (A) has the structural unit (III), solubility of the polymer (A) in the developer solution can be more appropriately adjusted, and as a result, the LWR performance and the CDU performance of the radiation-sensitive resin composition can be further improved. The structural unit (III) is exemplified by structural units represented by the following formulae, and the like.

-continued

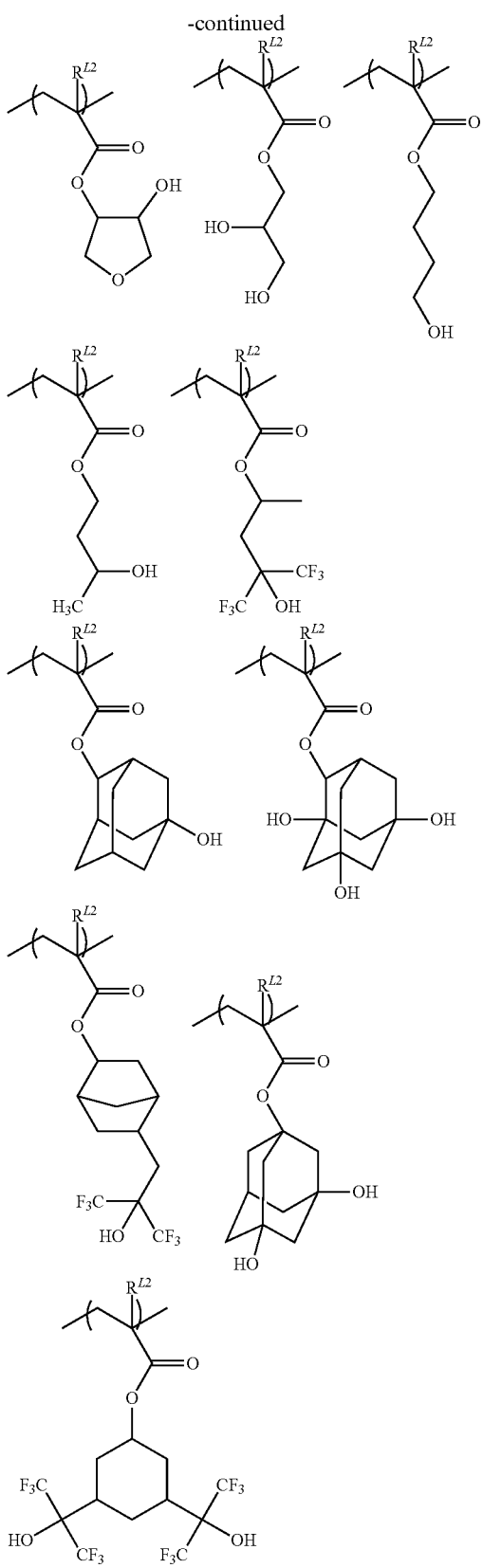

In each of the above formulae, $R^{L2}$ represents a hydrogen atom, a fluorine atom, a methyl group, or a trifluoromethyl group.

The lower limit of a proportion of the structural unit (III) contained with respect to total structural units in the polymer (A) is preferably 10 mol %, more preferably 15 mol %, and still more preferably 20 mol %. The upper limit of the proportion is preferably 45 mol %, more preferably 40 mol %, and still more preferably 35 mol %. When the proportion of the structural unit (III) falls within the above range, solubility of the polymer (A) in the developer solution can be further appropriately adjusted, and as a result, the LWR performance and the CDU performance of the radiation-sensitive resin composition can be further improved.

Structural Unit (IV)

The structural unit (IV) contains a phenolic hydroxyl group. The "phenolic hydroxyl group" as referred to herein is not limited to a hydroxy group directly linked to a benzene ring, and means any hydroxy group directly linked to an aromatic ring in general. In the case of using the ArF excimer laser beam, the KrF excimer laser beam, EUV, or the electron beam as the radioactive ray, when the polymer (A) has the structural unit (IV), sensitivity to the exposure light can be increased, and as a result, the LWR performance and the CDU performance of the radiation-sensitive resin composition can be further improved. The structural unit (IV) is exemplified by structural units represented by the following formula (P), and the like.

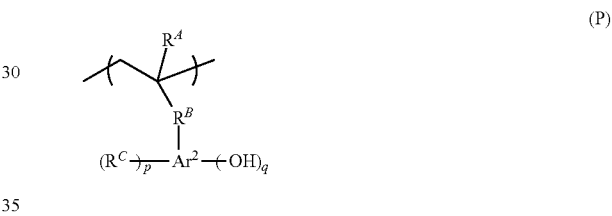

(P)

In the above formula (P), $R^A$ represents a hydrogen atom, a fluorine atom, a methyl group, or a trifluoromethyl group; $R^B$ represents a single bond, —O—, —COO—, or —CONH—; $Ar^2$ represents a group obtained by removing (p+q+1) hydrogen atoms from an aromatic ring of an arene having 6 to 20 ring atoms; p is an integer of 0 to 10, wherein in a case in which p is 1, $R^C$ is a halogen atom or a monovalent organic group having 1 to 20 carbon atoms, in a case in which p is no less than 2, a plurality of $R^C$s are identical or different from each other and each $R^C$ represents a halogen atom or a monovalent organic group having 1 to 20 carbon atoms, or no less than two of the plurality of $R^C$s taken together represent a part of a ring structure having 4 to 20 ring atoms constituted together with the carbon chain to which the no less than two $R^C$s bond; and q is an integer of 1 to 11, provided that a sum of p and q is no greater than 11.

In light of a degree of copolymerization of a monomer that gives the structural unit (IV), $R^A$ represents preferably a hydrogen atom or a methyl group, and more preferably a hydrogen atom. $R^B$ represents preferably a single bond or —COO—, and more preferably a single bond. Examples of the arene having 6 to 20 ring atoms that gives $Ar^e$ include benzene, naphthalene, anthracene, phenanthrene, tetracene, pyrene, and the like. Of these, benzene and naphthalene are preferred, and benzene is more preferred.

The monovalent organic group having 1 to 20 carbon atoms which may be represented by $R^C$ is exemplified by: a monovalent hydrocarbon group having 1 to 20 carbon atoms; a group that includes a divalent hetero atom-containing group between two adjacent carbon atoms or at the end of the atomic bonding side of the monovalent hydrocarbon group having 1 to 20 carbon atoms; a group obtained by substituting with a monovalent hetero atom-containing group, a part or all of hydrogen atoms included in the monovalent hydrocarbon group having 1 to 20 carbon atoms or the divalent hetero atom-containing group; and the like. $R^C$ represents preferably a hydrocarbon group, and more preferably an alkyl group. Examples of the ring structure having 4 to 20 ring atoms constituted by the no less than two of the plurality of $R^C$s taken together include, for example, alicyclic structures such as a cyclohexane structure, and the like. p is preferably 0 to 2, more preferably 0 or 1, and still more preferably 0. q is preferably 1 to 3, and more preferably 1 or 2.

Examples of the structural unit (IV) include structural units (hereinafter, may be also referred to as "structural units (IV-1) to (IV-12)") represented by the following formulae (P-1) to (P-12), and the like.

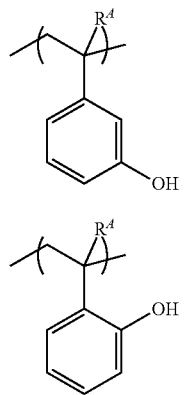
(P-1)

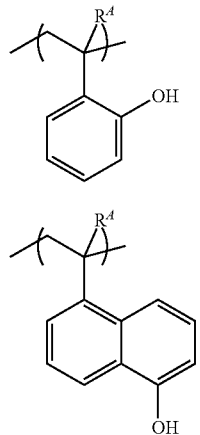
(P-2)

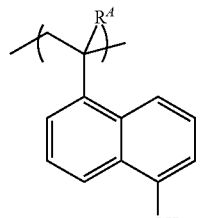
(P-3)

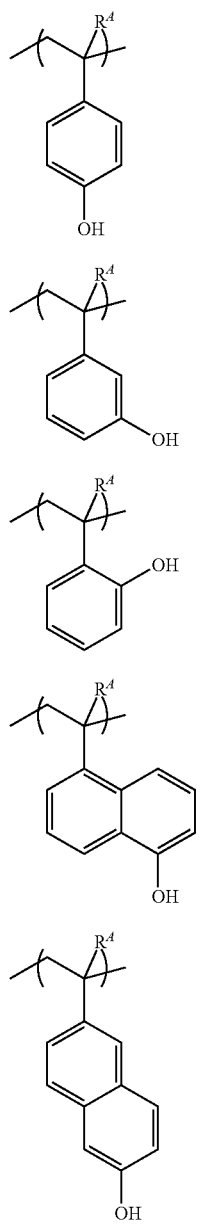
(P-4)

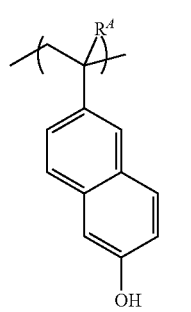
(P-5)

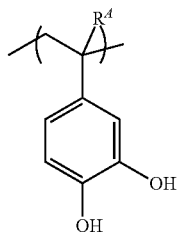
(P-6)

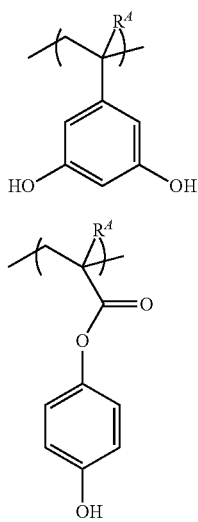
(P-7)

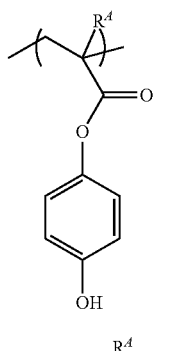
(P-8)

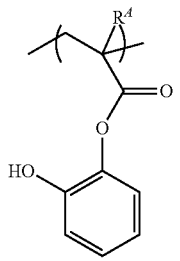
(P-9)

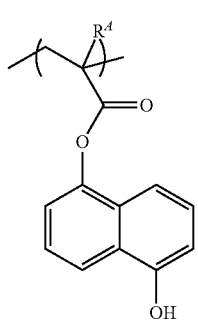
(P-10)

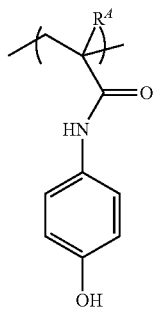
(P-11)

-continued

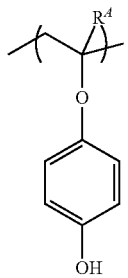
(P-12)

In each of the above formulae (P-1) to (P-12), $R^A$ is as defined in the above formula (P).

In a case in which the polymer (A) has the structural unit (IV), the lower limit of a proportion of the structural unit (IV) contained with respect to total structural units constituting the polymer (A) is preferably 10 mol %, more preferably 20 mol %, and particularly preferably 25 mol %. The upper limit of the proportion is preferably 50 mol %, more preferably 40 mol %, and particularly preferably 35 mol %. When the proportion of the structural unit (IV) falls within the above range, the LWR performance and the CDU performance of the radiation-sensitive resin composition can be further improved.

Other Structural Unit(s) The other structural unit(s) is/are exemplified by a structural unit that includes an acid-nonlabile hydrocarbon group, and the like. Examples of the acid-nonlabile hydrocarbon group include a monovalent chain hydrocarbon group bonded to an oxy group of —COO—, a monovalent alicyclic hydrocarbon group, and the like. In the case in which the polymer (A) has the other structural unit(s), the upper limit of a proportion of the other structural unit(s) is preferably 30 mol %, and more preferably 20 mol %. The upper limit of the proportion is, for example, 1 mol %.

The polymer (A) preferably has the structural unit (III). In other words, the polymer (A) preferably has the structural unit (III) in addition to the structural unit (I). When the polymer (A) thus has the structural unit (III), the LWR performance and the CDU performance can be further improved.

The lower limit of a polystyrene-equivalent weight average molecular weight (Mw) of the polymer (A) as determined by gel permeation chromatography (GPC) is preferably 2,000, more preferably 3,000, still more preferably 4,000, and particularly preferably 5,000. The upper limit of the Mw is preferably 30,000, more preferably 20,000, still more preferably 15,000, and particularly preferably 10,000. When the Mw falls within the above range, the coating characteristics of the radiation-sensitive resin composition can be improved, and as a result, the LWR performance and the CDU performance can be further improved.

The upper limit of a ratio (Mw/Mn) of the Mw to a polystyrene-equivalent number average molecular weight (Mn) of the polymer (A) as determined by GPC is preferably 3.00, more preferably 2.50, still more preferably 2.00, and particularly preferably 1.85. The lower limit of the ratio is typically 1.00, and preferably 1.10.

It is to be noted that the Mw and Mn of the polymer herein are values determined by gel permeation chromatography (GPC) under the following conditions.

GPC columns: "G2000 HXL"×2, "G3000 HXL"×1, and "G4000 HXL"×1, available from Tosoh Corporation;
elution solvent: tetrahydrofuran;
flow rate: 1.0 mL/min;
sample concentration: 1.0% by mass;
amount of injected sample: 100 µL;
column temperature: 40° C.;
detector: differential refractometer; and
standard substance: mono-dispersed polystyrene The polymer (A) can be synthesized by, for example, polymerizing a monomer that gives each structural unit according to a well-known procedure.

The lower limit of a proportion of the polymer (A) with respect to all components of the radiation-sensitive resin composition other than the solvent (D) is preferably 50% by mass, more preferably 70% by mass, and still more preferably 80% by mass.

(B) Acid Generator

The acid generator (B) is a substance which generates an acid by irradiation with a radioactive ray. Examples of the radioactive ray include: electromagnetic waves such as visible light rays, ultraviolet rays, far ultraviolet rays, EUV, X-rays, and γ-rays; charged particle rays such as electron beams and α-rays; and the like. The acid-labile group of the polymer (A) is disassociated by an action of the acid generated from the acid generator (B), generating a carboxy group or a phenolic hydroxyl group and changing the solubility of the polymer (A) in the developer solution; accordingly, a resist pattern can be formed from the radiation-sensitive resin composition. The acid generator (B) may be contained in the radiation-sensitive resin composition either in the form of a low-molecular-weight compound (hereinafter, may be also referred to as "(B) acid generating agent" or "acid generating agent (B)") or in the form of an acid generator incorporated as a part of a polymer such as the polymer (A), or may be in a combination of both these forms.

The lower limit of a temperature at which the acid disassociates the acid-labile group is preferably 60° C., more preferably 70° C., and still more preferably 80° C. The upper limit of the temperature is preferably 130° C., more preferably 120° C., and still more preferably 110° C. The lower limit of a time period for the acid to disassociate the acid-labile group is preferably 10 sec, and more preferably 1 min. The upper limit of the time period is preferably 10 min, and more preferably 2 min.

Examples of the acid generated from the acid generator (B) include sulfonic acid, imidic acid, and the like.

The acid generating agent (B) is exemplified by an onium salt compound, an N-sulfonyloxyimide compound, a sulfonimide compound, a halogen-containing compound, a diazoketone compound, and the like. Examples of the onium salt compound include sulfonium salts, tetrahydrothiophenium salts, iodonium salts, phosphonium salts, diazonium salts, pyridinium salts, and the like. Specific examples of the acid generating agent (B) include compounds disclosed in paragraphs [0080] to [0113] of Japanese Unexamined Patent Application, Publication No. 2009-134088, and the like.

The acid generating agent (B) that generates sulfonic acid by irradiation with a radioactive ray is exemplified by a compound (hereinafter, may be also referred to as "compound (3)") represented by the following formula (3), and the like. It is considered that when the acid generating agent (B) has the following structure, a diffusion length of the generated acid in the resist film is more appropriately shortened by an interaction with the polymer (A) and the like, and as a result, the LWR performance and the CDU performance of the radiation-sensitive resin composition can be further improved.

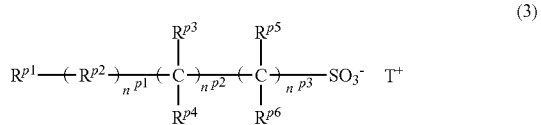

(3)

In the above formula (3), $R^{p1}$ represents a monovalent group containing a ring structure having 5 or more ring atoms; $R^{p2}$ represents a divalent linking group; $R^{p3}$ and $R^{p4}$ each independently represent a hydrogen atom, a fluorine atom, a monovalent hydrocarbon group having 1 to 20 carbon atoms, or a monovalent fluorinated hydrocarbon group having 1 to 20 carbon atoms; $R^{p5}$ and $R^{p6}$ each independently represent a fluorine atom or a monovalent fluorinated hydrocarbon group having 1 to 20 carbon atoms; $n^{p1}$ is an integer of 0 to 10; $n^{p2}$ is an integer of 0 to 10; and $n^{p3}$ is an integer of 0 to 10, wherein a sum of $n^{p1}$, $n^{p2}$, and $n^{p3}$ is no less than 1 and no greater than 30, and wherein in a case in which $n^{p1}$ is no less than 2, a plurality of $R^{p2}$s are identical or different from each other, in a case in which $n^{p2}$ is no less than 2, a plurality of $R^{p3}$s are identical or different from each other and a plurality of $R^{p4}$s are identical or different from each other, and in a case in which $n^{p3}$ is no less than 2, a plurality of $R^{p5}$s are identical or different from each other and a plurality of $R^{p6}$s are identical or different from each other; and $T^+$ represents a monovalent radiation-sensitive onium cation.

The monovalent group containing a ring structure having 5 or more ring atoms which is represented by $R^{p1}$ is exemplified by: a monovalent group containing an alicyclic structure having 5 or more ring atoms; a monovalent group containing an aliphatic heterocyclic structure having 5 or more ring atoms; a monovalent group containing an aromatic ring structure having 5 or more ring atoms; a monovalent group containing an aromatic heterocyclic structure having 5 or more ring atoms; and the like.

Examples of the alicyclic structure having 5 or more ring atoms include:

monocyclic saturated alicyclic structures such as a cyclopentane structure, a cyclohexane structure, a cycloheptane structure, a cyclooctane structure, a cyclononane structure, a cyclodecane structure, and a cyclododecane structure;

monocyclic unsaturated alicyclic structures such as a cyclopentene structure, a cyclohexene structure, a cycloheptene structure, a cyclooctene structure, and a cyclodecene structure;

polycyclic saturated alicyclic structures such as a norbornane structure, an adamantane structure, a tricyclodecane structure, and a tetracyclododecane structure;

polycyclic unsaturated alicyclic structures such as a norbornene structure and a tricyclodecene structure; and the like.

Examples of the aliphatic heterocyclic structure having 5 or more ring atoms include:

lactone structures such as a hexanolactone structure and a norbornanelactone structure;

sultone structures such as a hexanosultone structure and a norbornanesultone structure;

oxygen atom-containing heterocyclic structures such as an oxacycloheptane structure and an oxanorbornane structure;

nitrogen atom-containing heterocyclic structures such as an azacyclohexane structure and a diazabicyclooctane structure;

sulfur atom-containing heterocyclic structures such as a thiacyclohexane structure and a thianorbornane structure; and the like.

Examples of the aromatic ring structure having 5 or more ring atoms include a benzene structure, a naphthalene structure, a phenanthrene structure, an anthracene structure, and the like.

Examples of the aromatic heterocyclic structure having 5 or more ring atoms include:

oxygen atom-containing heterocyclic structures such as a furan structure, a pyran structure, a benzofuran structure, and a benzopyran structure;

nitrogen atom-containing heterocyclic structures such as a pyridine structure, a pyrimidine structure, and an indole structure; and the like.

The lower limit of the number of ring atoms of the ring structure included in $R^{p1}$ is preferably 6, more preferably 8, still more preferably 9, and particularly preferably 10. The upper limit of the number of ring atoms is preferably 15, more preferably 14, still more preferably 13, and particularly preferably 12. When the number of ring atoms falls within the above range, the aforementioned diffusion length of the acid can be more properly reduced, and as a result, the LWR performance and the CDU performance of the radiation-sensitive resin composition can be further improved.

A part or all of hydrogen atoms included in the ring structure of $R^{p1}$ may be substituted with a substituent. Examples of the substituent include: halogen atoms such as a fluorine atom, a chlorine atom, a bromine atom, and an iodine atom; a hydroxy group; a carboxy group; a cyano group; a nitro group; an alkoxy group; an alkoxycarbonyl group; an alkoxycarbonyloxy group; an acyl group; an acyloxy group; and the like. Of these, a hydroxy group is preferred.

$R^{p1}$ represents: preferably a monovalent group containing an alicyclic structure having 5 or more ring atoms, or a monovalent group containing an aliphatic heterocyclic structure having 5 or more ring atoms; more preferably a monovalent group containing an alicyclic structure having 9 or more ring atoms, or a monovalent group containing an aliphatic heterocyclic structure having 9 or more ring atoms; still more preferably an adamantyl group, a hydroxyadamantyl group, a norbornanelactone-yl group, a norbornanesultone-yl group, or a 5-oxo-4-oxatricyclo[4.3.1.1$^{3,8}$]undecan-yl group; and particularly preferably an adamantyl group.

Examples of the divalent linking group represented by $R^{p2}$ include a carbonyl group, an ether group, a carbonyloxy group, a sulfide group, a thiocarbonyl group, a sulfonyl group, a divalent hydrocarbon group, and the like. Of these, the carbonyloxy group, the sulfonyl group, an alkanediyl group, or a divalent alicyclic saturated hydrocarbon group is preferred; the carbonyloxy group or the divalent alicyclic saturated hydrocarbon group is more preferred; the carbonyloxy group or a norbornanediyl group is still more preferred, and the carbonyloxy group is particularly preferred.

The monovalent hydrocarbon group having 1 to 20 carbon atoms which may be represented by $R^{p3}$ or $R^{p4}$ is exemplified by an alkyl group having 1 to 20 carbon atoms, and the like. The monovalent fluorinated hydrocarbon group having 1 to 20 carbon atoms which may be represented by $R^{p3}$ or $R^{p4}$ is exemplified by a fluorinated alkyl group having 1 to 20 carbon atoms, and the like. $R^{p3}$ and $R^{p4}$ each independently represent: preferably a hydrogen atom, a fluorine atom, or a fluorinated alkyl group; more preferably a fluorine atom or a perfluoroalkyl group; and still more preferably a fluorine atom or a trifluoromethyl group.

The monovalent fluorinated hydrocarbon group having 1 to 20 carbon atoms which may be represented by $R^{p5}$ or $R^{p6}$ is exemplified by a fluorinated alkyl group having 1 to 20 carbon atoms, and the like. $R^{p5}$ and $R^{p6}$ each independently represent preferably a fluorine atom or a fluorinated alkyl group, more preferably a fluorine atom or a perfluoroalkyl group, still more preferably a fluorine atom or a trifluoromethyl group, and particularly preferably a fluorine atom.

In the above formula (3), $n^{p1}$ is preferably 0 to 5, more preferably 0 to 3, still more preferably 0 to 2, and particularly preferably 0 or 1; $n^{p2}$ is preferably 0 to 5, more preferably 0 to 2, still more preferably 0 or 1, and particularly preferably 0; the lower limit of $n^{p3}$ is preferably 1 and more preferably 2. When $n^{p3}$ is no less than 1, the strength of the acid generated from the compound (3) can be increased, and consequently the LWR performance and the CDU performance of the radiation-sensitive resin composition can be further improved. The upper limit of $n^{p3}$ is preferably 4, more preferably 3, and still more preferably 2; the lower limit of a sum of $n^{p1}$, $n^{p2}$, and $n^{p3}$ is preferably 2, and more preferably 4; and the upper limit of the sum of $n^{p1}$, $n^{p2}$, and $n^{p3}$ is preferably 20, and more preferably 10.

The monovalent radiation-sensitive onium cation which may be represented by $T^+$ is exemplified by a cation represented by the following formula (r-a) (hereinafter, may be also referred to as "cation (r-a)"), a cation represented by the following formula (r-b) (hereinafter, may be also referred to as "cation (r-b)"), a cation represented by the following formula (r-c) (hereinafter, may be also referred to as "cation r-c"), and the like.

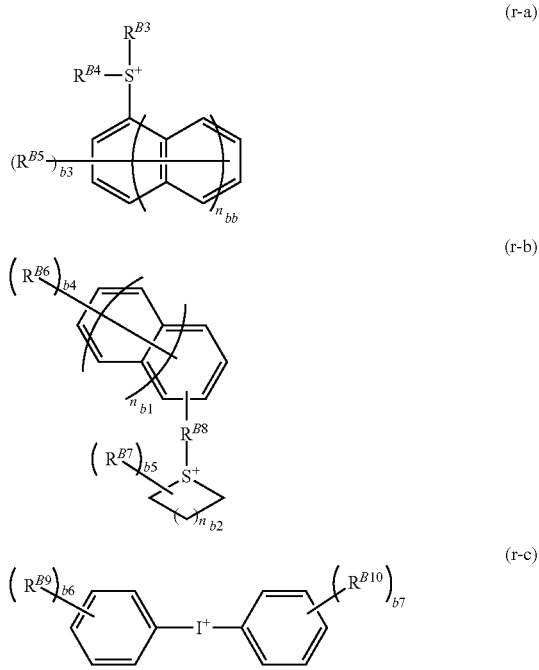

In the above formula (r-a), $R^{B3}$ and $R^{B4}$ each independently represent a monovalent organic group having 1 to 20 carbon atoms, or $R^{B3}$ and $R^{B4}$ taken together represent a part of a ring structure having 4 to 20 ring atoms constituted together with the sulfur atom to which $R^{B3}$ and $R^{B4}$ bond; b3 is an integer of 0 to 11, wherein in a case in which b3 is 1, $R^{B5}$ represents a monovalent organic group having 1 to 20 carbon atoms, a hydroxy group, a nitro group, or a halogen atom, and in a case in which b3 is no less than 2, a plurality of $R^{B5}$s are identical or different from each other, and each $R^{B5}$ represents a monovalent organic group having 1 to 20 carbon atoms, a hydroxy group, a nitro group, or a halogen atom, or the plurality of R's taken together represent a part of a ring structure having 4 to 20 ring atoms constituted together with the carbon chain to which the plurality of $R^{B5}$s bond; and $n_{bb}$ is an integer of 0 to 3.

The monovalent organic group having 1 to 20 carbon atoms which may be represented by $R^{B3}$, $R^{B4}$, or $R^{B5}$ is exemplified by: a monovalent hydrocarbon group having 1 to 20 carbon atoms; a monovalent group (g) that includes a divalent hetero atom-containing group between two adjacent carbon atoms of the monovalent hydrocarbon group having 1 to 20 carbon atoms, or at an end of the monovalent hydrocarbon group having 1 to 20 carbon atoms; a monovalent group obtained by substituting with a hetero atom-containing group, a part or all of hydrogen atoms included in the monovalent hydrocarbon group having 1 to 20 carbon atoms or the monovalent group (g); and the like.

$R^{B3}$ and $R^{B4}$ each represent preferably a monovalent unsubstituted hydrocarbon group having 1 to 20 carbon atoms or a hydrocarbon group obtained therefrom by substituting a hydrogen atom included therein with a substituent, more preferably a monovalent unsubstituted aromatic hydrocarbon group having 6 to 18 carbon atoms or an aromatic hydrocarbon group obtained therefrom by substituting a hydrogen atom included therein with a substituent, still more preferably a substituted or unsubstituted phenyl group, and particularly preferably an unsubstituted phenyl group.

The substituent which may substitute for the hydrogen atom included in the monovalent hydrocarbon group having 1 to 20 carbon atoms which may be represented by $R^{B3}$ or $R^{B4}$ is preferably a substituted or unsubstituted monovalent hydrocarbon group having 1 to 20 carbon atoms, $-OSO_2-R^{Bk}$, $-SO_2-R^{Bk}$, $-OR^{Bk}$, $-COOR^{Bk}$, $-O-CO-R^{Bk}$, $-O-R^{Bk2}-COOR^{Bk}$, $-R^{Bk2}-CO-R^{Bk}$, or $-S-R^{Bk}$, wherein $R^{Bk}$ represents a monovalent hydrocarbon group having 1 to 10 carbon atoms; and R' represents a single bond or a divalent hydrocarbon group having 1 to 10 carbon atoms.

$R^{B5}$ represents preferably a substituted or unsubstituted monovalent hydrocarbon group having 1 to 20 carbon atoms, $-OSO_2-R^{Bk}$, $-SO_2-R^{Bk}$, $-OR^{Bk}$, $COOR^{Bk}$, $-O-CO-R^{Bk}$, $-O-R^{Bk2}-COOR^{Bk}$, $-R^{Bk2}-CO-R^{Bk}$, or $-S-R^{Bk}$, wherein $R^{Bk}$ represents a monovalent hydrocarbon group having 1 to 10 carbon atoms; and $R^{Bk2}$ represents a single bond or a divalent hydrocarbon group having 1 to 10 carbon atoms.

In the above formula (r-b), b4 is an integer of 0 to 9, wherein in a case in which b4 is 1, $R^{B6}$ represents a monovalent organic group having 1 to 20 carbon atoms, a hydroxy group, a nitro group, or a halogen atom, and in a case in which b4 is no less than 2, a plurality of $R^{B6}$s are identical or different from each other, and each $R^{B6}$ represents a monovalent organic group having 1 to 20 carbon atoms, a hydroxy group, a nitro group, or a halogen atom, or the plurality of $R^{B6}$s taken together represent a part of a ring structure having 4 to 20 ring atoms constituted together with the carbon chain to which the plurality of $R^{B6}$s bond; b5 is an integer of 0 to 10, wherein in a case in which b5 is 1, $R^{B7}$ represents a monovalent organic group having 1 to 20 carbon atoms, a hydroxy group, a nitro group, or a halogen atom, and in a case in which b5 is no less than 2, a plurality of $R^{B7}$s are identical or different from each other, and each $R^{B7}$ represents a monovalent organic group having 1 to 20 carbon atoms, a hydroxy group, a nitro group, or a halogen atom, or the plurality of $R^{B7}$s taken together represent a part of a ring structure having 3 to 20 ring atoms constituted together with the carbon atom or the carbon chain to which the plurality of $R^{B7}$s bond; $n_{b2}$ is an integer of 0 to 3; $R^{B8}$ represents a single bond or a divalent organic group having 1 to 20 carbon atoms; and $n_{b1}$ is an integer of 0 to 2.

$R^{B6}$ and $R^{B7}$ each represent preferably a substituted or unsubstituted monovalent hydrocarbon group having 1 to 20 carbon atoms, $-OR^{Bk}$, $-COOR^{Bk}$, $-O-CO-R^{Bk}$, $-O-R^{Bk2}-COOR^{Bk}$ or $-R^{Bk2}-CO-R^{Bk}$, wherein $R^{Bk}$ represents a monovalent hydrocarbon group having 1 to 10 carbon atoms; and R' represents a single bond or a divalent hydrocarbon group having 1 to 10 carbon atoms.

In the above formula (r-c), b6 is an integer of 0 to 5, wherein in a case in which b6 is 1, $R^{B9}$ represents a monovalent organic group having 1 to 20 carbon atoms, a hydroxy group, a nitro group, or a halogen atom, and in a case in which b6 is no less than 2, a plurality of $R^{B9}$s are identical or different from each other, and each $R^{B9}$ represents a monovalent organic group having 1 to 20 carbon atoms, a hydroxy group, a nitro group, or a halogen atom, or the plurality of R's taken together represent a part of a ring structure having 4 to 20 ring atoms constituted together with the carbon chain to which the plurality of $R^{B9}$s bond; and b7 is an integer of 0 to 5, wherein in a case in which b7 is 1, $R^{B10}$ represents a monovalent organic group having 1 to 20 carbon atoms, a hydroxy group, a nitro group, or a halogen atom, and in a case in which b7 is no less than 2, a plurality of $R^{B10}$s are identical or different from other each, and each $R^{B10}$ represents a monovalent organic group having 1 to 20 carbon atoms, a hydroxy group, a nitro group, or a halogen atom, or the plurality of $R^{B10}$s taken together represent a part of a ring structure having 4 to 20 ring atoms constituted together with the carbon chain to which the plurality of $R^{B10}$s bond.

$R^{B9}$ and $R^{B10}$ each represent preferably a substituted or unsubstituted monovalent hydrocarbon group having 1 to 20 carbon atoms, $-OSO_2-R^{Bk}$, $-SO_2-R^{Bk}$, $-OR^{Bk}$, $-COOR^{Bk}$, $-O-CO-R^{Bk}$, $-O-R^{Bk2}-COOR^{Bk}$, $-R^{Bk2}-CO-R^{Bk}$, $-R^{Bk}$, or a ring structure constituted from at least two selected from these groups taken together, wherein $R^{Bk}$ represents a monovalent hydrocarbon group having 1 to 10 carbon atoms; and $R^{Bk2}$ represents a single bond or a divalent hydrocarbon group having 1 to 10 carbon atoms.

Examples of the monovalent hydrocarbon group having 1 to 20 carbon atoms which may be represented by $R^{B5}$, $R^{B6}$, $R^{B7}$, $R^{B9}$, or $R^{B10}$ include: linear alkyl groups such as a methyl group, an ethyl group, a n-propyl group, and an n-butyl group; branched alkyl groups such as an i-propyl group, an i-butyl group, a sec-butyl group, and a t-butyl group; aryl groups such as a phenyl group, a tolyl group, a xylyl group, a mesityl group, and a naphthyl group; aralkyl groups such as a benzyl group and a phenethyl group; and the like.

Examples of the divalent organic group which may be represented by $R^{B8}$ include groups obtained by removing one hydrogen atom from the monovalent organic groups having 1 to 20 carbon atoms exemplified as $R^{B3}$, $R^{B4}$, and $R^{B5}$ in the above formula (r-a), and the like.

Examples of the substituent which may substitute for the hydrogen atom included in the hydrocarbon group which may be represented by $R^{B5}$, $R^{B6}$, $R^{B7}$, $R^{B9}$ or $R^{B10}$ include halogen atoms such as a fluorine atom; a hydroxy group; a carboxy group; a cyano group; a nitro group; an alkoxy group; an alkoxycarbonyl group; an alkoxycarbonyloxy group; an acyl group; an acyloxy group; and the like. Of these, a halogen atom is preferred, and a fluorine atom is more preferred.

$R^{B5}$, $R^{B6}$, $R^{B7}$, $R^{B9}$ and $R^{B10}$ each represent preferably an unsubstituted linear or branched monovalent alkyl group, a monovalent fluorinated alkyl group, an unsubstituted monovalent aromatic hydrocarbon group, $-OSO_2-R^{Bk}$ or $-SO_2-R^{Bk}$, more preferably a fluorinated alkyl group or an unsubstituted monovalent aromatic hydrocarbon group, and still more preferably a fluorinated alkyl group, wherein $R^{Bk}$ represents a monovalent hydrocarbon group having 1 to 10 carbon atoms.

In the above formula (r-a), b3 is preferably 0 to 2, more preferably 0 or 1, and still more preferably 0; and $n_{bb}$ is preferably 0 or 1, and more preferably 0. In the above formula (r-b), b4 is preferably 0 to 2, more preferably 0 or 1, and still more preferably 0; b5 is preferably 0 to 2, more preferably 0 or 1, and still more preferably 0; $n_{b2}$ is preferably 2 or 3, and more preferably 2; and $n_{b1}$ is preferably 0 or 1, and more preferably 0. In the above formula (r-c), b6 and b7 are each preferably 0 to 2, more preferably 0 or 1, and still more preferably 0.

Of these, $T^+$ preferably represents the cation (r-a), and more preferably represents a triphenylsulfonium cation.

The acid generating agent (B) is exemplified by: compounds represented by the following formulae (3-1) to (3-16) (hereinafter, may be also referred to as "compounds (3-1) to (3-16)") as an acid generating agent which generates sulfonic acid; compounds represented by the following formulae (4-1) to (4-3) (hereinafter, may be also referred to as "compounds (4-1) to (4-3)") as an acid generating agent which generates imidic acid; and the like.

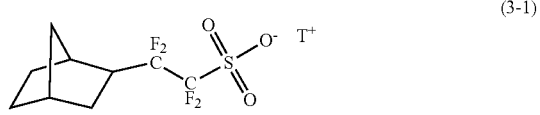

(3-1)

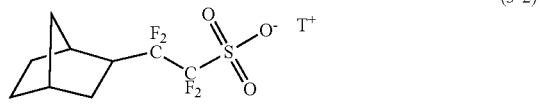

(3-2)

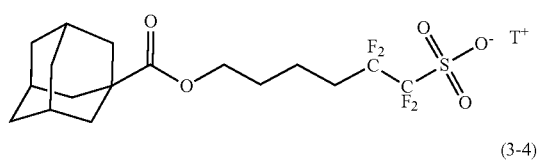

(3-3)

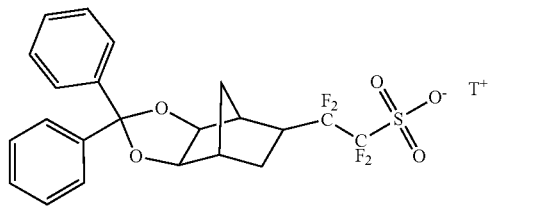

(3-4)

(3-5) 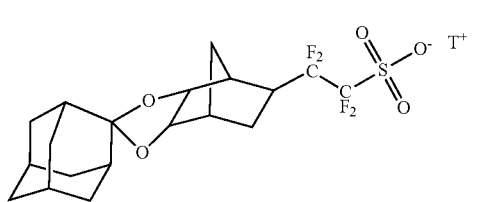

(3-6) 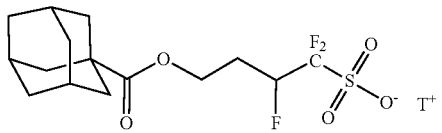

(3-7) 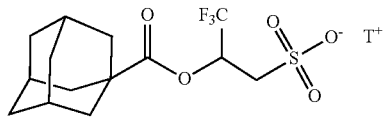

(3-8) 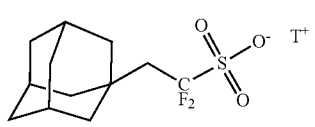

(3-9) 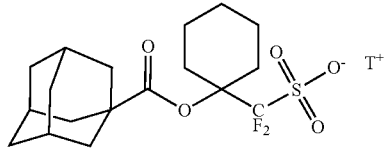

(3-10) 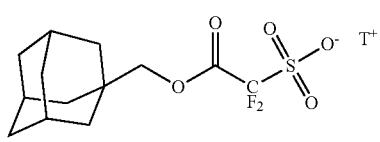

(3-11) 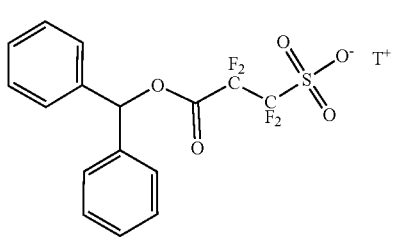

(3-12) 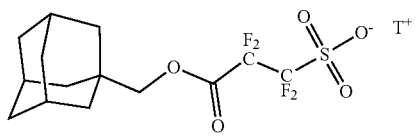

(3-13) 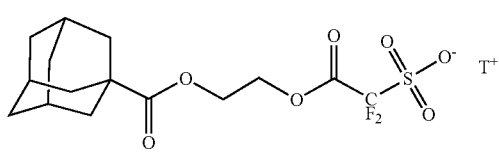

(3-14) 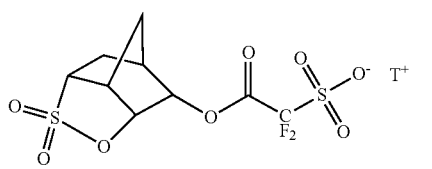

(3-15) 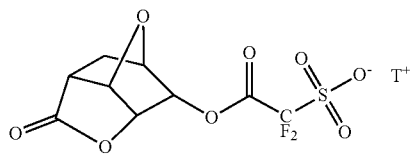

(3-16) 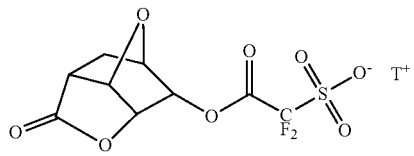

(4-1) 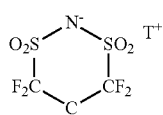

(4-2) 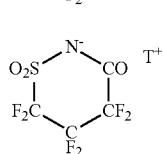

(4-3) 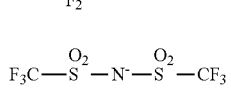

In the above formulae (3-1) to (3-16) and (4-1) to (4-3), T⁺ represents a monovalent radiation-sensitive onium cation.

Furthermore, the acid generator (B) may be also exemplified as a polymer, with the structure of the acid generator being incorporated as a part of the polymer (A).

In the case in which the acid generator (B) is the acid generating agent (B), the lower limit of a content of the acid generating agent (B) with respect to 100 parts by mass of the polymer (A) is preferably 0.1 parts by mass, more preferably 1 part by mass, and still more preferably 10 parts by mass. The upper limit of the content is preferably 50 parts by mass, more preferably 30 parts by mass, and still more preferably 20 parts by mass. When the content of the acid generating agent (B) falls within the above range, the sensitivity of the radiation-sensitive resin composition to exposure light can be further improved, and the LWR performance and the CDU performance can be further improved. The radiation-sensitive resin composition may contain one, or two or more types of the acid generator (B).

(C) Compound

The radiation-sensitive resin composition contains the compound (C). The compound (C) may be used as the acid diffusion control agent. In the case in which the radiation-sensitive resin composition contains the acid generator (B), the compound (C) is able to control a diffusion phenomenon of the acid generated from the acid generator (B) and the like in the resist film upon exposure, thereby serving to inhibit unwanted chemical reactions in an un-exposed region. Furthermore, the sensitivity to exposure light, the LWR performance, and the CDU performance can be improved.

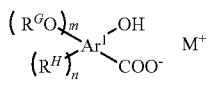
(1)

In the above formula (1), $Ar^1$ represents a group obtained by removing (m+n+2) hydrogen atoms from an aromatic ring of an arene having 6 to 30 carbon atoms;

—OH and —COO— are bonded at ortho positions to each other on a same benzene ring on $Ar^1$;

m is an integer of 1 to 16, wherein in a case in which m is 1, $R^G$ is a group represented by the following formula (V-1), a group represented by the following formula (V-2), a group containing a lactone structure, a group containing a cyclic carbonate structure, a group containing a sultone structure, a group containing a ketonic carbonyl group, a group containing a thiocarbonate group, or a group containing a group represented by the following formula (V-3), and in a case in which m is no less than 2, a plurality of $R^G$s are identical or different from each other and are each a group represented by the following formula (V-1), a group represented by the following formula (V-2), a group containing a lactone structure, a group containing a cyclic carbonate structure, a group containing a sultone structure, a group containing a ketonic carbonyl group, a group containing a thiocarbonate group, or a group containing a group represented by the following formula (V-3), or the plurality of $R^G$s taken together represent a part of a ring structure having 5 to 20 ring atoms constituted together with the atomic chain to which the plurality of $R^G$s bond;

n is an integer of 0 to 15, wherein in a case in which n is 1, $R^H$ is a substituted or unsubstituted monovalent hydrocarbon group having 1 to 20 carbon atoms, or a halogen atom, and in a case in which n is no less than 2, a plurality of $R^H$s are identical or different from each other, and each represents a substituted or unsubstituted monovalent hydrocarbon group having 1 to 20 carbon atoms, or a halogen atom, or the plurality of $R^H$s taken together represent a part of an alicyclic structure having 4 to 20 ring atoms constituted together with the carbon chain to which the plurality of $R^H$s bond, and wherein a sum of m and n is no greater than 16; and $M^+$ is a monovalent radiation-sensitive cation.

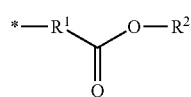
(V-1)

In the above formula (V-1), $R^1$ represents a substituted or unsubstituted divalent hydrocarbon group having 1 to 20 carbon atoms;

$R^2$ represents a monovalent organic group having 1 to 20 carbon atoms; and

* denotes a binding site to an oxygen atom adjacent to $Ar^1$ in the above formula (1).

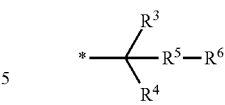
(V-2)

In the above formula (V-2), $R^3$ and $R^4$ each independently represent a hydrogen atom or a substituted or unsubstituted monovalent hydrocarbon group having 1 to 20 carbon atoms;

$R^5$ represents —O— or —S—; and $R^6$ represents a monovalent organic group having 1 to 20 carbon atoms, or $R^4$, $R^5$, and $R^6$ taken together represent a part of a ring structure having 4 to 20 ring atoms constituted together with the atomic chain to which $R^4$, $R^5$, and $R^6$ bond; and

* denotes a binding site to an oxygen atom adjacent to $Ar^1$ in the above formula (1).

(V-3)

In the above formula (V-3), $R^7$ represents a fluorine atom or a monovalent fluorinated hydrocarbon group having 1 to 20 carbon atoms;

$R^8$ represents a hydrogen atom, a fluorine atom, or a monovalent organic group having 1 to 20 carbon atoms;

$R^9$ represents a hydrogen atom or a monovalent organic group having 1 to 20 carbon atoms; and

** denotes a binding site to an oxygen atom adjacent to $Ar^1$ in the above formula (1) or to a part other than the group represented by the above formula (V-3) in $R^G$.

Examples of the arene having 6 to 30 ring atoms which may be represented by $Ar^1$ in the above formula (1) include benzene, naphthalene, anthracene, phenanthrene, tetracene, pyrene, and the like. Of these, benzene and naphthalene are preferred, and benzene is more preferred. Examples of the monovalent hydrocarbon group having 1 to 20 carbon atoms which may be represented by $R^H$ in the above formula (1) include the monovalent hydrocarbon group represented by $R^X$ or the like in the above formula (2-1A) of the structural unit (I), and the like.

Of the group containing the lactone structure, the group containing the cyclic carbonate structure, the group containing the sultone structure, the group containing the ketonic carbonyl group, and the group containing the thiocarbonate group, each of which gives $R^G$, the group containing the lactone structure, the group containing the cyclic carbonate structure, and the group containing the sultone structure are preferred. When $R^G$ is thus the group containing the lactone structure, the group containing the cyclic carbonate structure, or the group containing the sultone structure, the CDU performance can be further improved.

Examples of the divalent hydrocarbon group having 1 to 20 carbon atoms which may be represented by $R^1$ in the above formula (V-1) include a group obtained by removing one hydrogen atom from the monovalent hydrocarbon groups exemplified as $R^X$ or the like in the above formula (2-1A) of the structural unit (I), and the like. Examples of the monovalent organic group having 1 to 20 carbon atoms which may be represented by $R^2$ include the monovalent organic groups exemplified as $R^{B3}$ and the like in the above formula (r-a) of the acid generator (B), and the like.

Examples of the monovalent hydrocarbon group having 1 to 20 carbon atoms which may be represented by $R^3$ or $R^4$ in the above formula (V-2) include the monovalent hydrocarbon groups exemplified as $R^X$ and the like in the above formula (2-1A) of structural unit (I), and the like. $R^5$ represents —O— or —S—, and preferably represents —O—. Examples of the monovalent organic group having 1 to 20 carbon atoms which may be represented by $R^6$ include the monovalent organic groups exemplified as $R^{B3}$ and the like in the above formula (r-a) of the acid generator (B), and the like.

Examples of the monovalent fluorinated hydrocarbon group having 1 to 20 carbon atoms which may be represented by $R^7$ in the above formula (V-3) include the monovalent fluorinated hydrocarbon groups exemplified as $R^{P5}$ and the like in the above formula (3) of the acid generator (B), and the like. Examples of the monovalent organic group having 1 to 20 carbon atoms which may be represented by $R^8$ include the monovalent organic groups exemplified as $R^{B3}$ and the like in the above formula (r-a) of the acid generator (B), and the like. Examples of the monovalent organic group having 1 to 20 carbon atoms which may be represented by $R^9$ include the monovalent organic groups exemplified as $R^{B3}$ and the like in the above formula (r-a) of the acid generator (B), and the like.

In the above formula (1), m is preferably 1 or 2.

In the above formula (1), $R^G$ is preferably a group represented by the above formula (V-1). In the formula (V-1), $R^2$ is preferably a monovalent organic group having 1 to 20 carbon atoms and having a ring structure with 3 to 12 ring atoms. When $R^G$ is a group represented by the above formula (V-1) and $R^2$, included therein, has the aforementioned ring structure, the sensitivity to exposure light can be further improved. Such an $R^G$ is preferably a monovalent hydrocarbon group having 1 to 20 carbon atoms and having an alicyclic structure with 3 to 12 ring atoms, and more preferably a group having an acid-labile group, the group being a monovalent hydrocarbon group having 1 to 20 carbon atoms and having an alicyclic structure with 3 to 12 rings. The acid-labile group is a group that substitutes for a hydrogen atom of a carboxy group, and is dissociable by an action of an acid.

In the case in which m in the above formula (1) is 2, two $R^G$s each independently represent a group represented by the above formula (V-1). When the two $R^G$s thus represent the group represented by the above formula (V-1), the sensitivity to exposure light, the LWR performance, and the CDU performance can be further improved.

$M^+$ in the above formula (1) is exemplified by the monovalent radiation-sensitive cation represented by $T^+$ of the acid generator (B), and the like.

$M^+$ in the above formula (1) preferably represents a monovalent radiation-sensitive cation having a fluorine atom. When $M^+$ thus represents the monovalent radiation-sensitive cation having a fluorine atom, the sensitivity to exposure light can be further improved.

$M^+$ in the above formula (1) preferably represents a cation represented by the above formula (r-a) of the acid generator (B). It is preferable that in the formula (r-a), $R^{B3}$ and $R^{B4}$ each represent a monovalent organic group, or $R^{B3}$ and $R^{B4}$ taken together represent a part of a ring structure having 4 to 20 ring atoms constituted together with the sulfur atom to which $R^{B3}$ and $R^{B4}$ bond; $n^{bb}$ is 0; $b^3$ is 1; and $R^{B5}$ represents a monovalent hydrocarbon group having 1 to 20 carbon atoms. When $M^+$ thus represents the cation represented by the above formula (r-a), the sensitivity to exposure light, the LWR performance, and the CDU performance can be further improved.

The compound (C) is exemplified by compounds represented by the following formulae (1-1) to (1-18) (hereinafter, may be also referred to as "compounds (1-1) to (1-18)"), and the like.

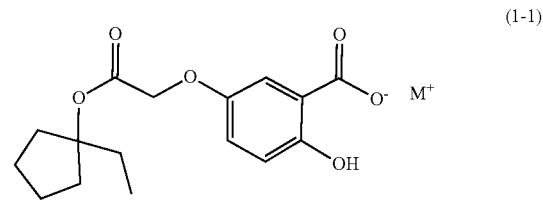

(1-1)

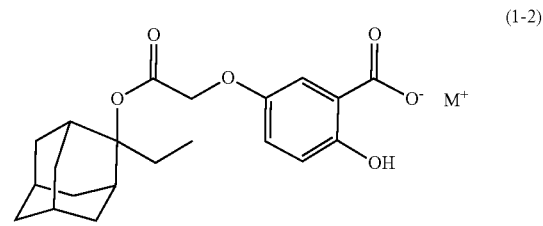

(1-2)

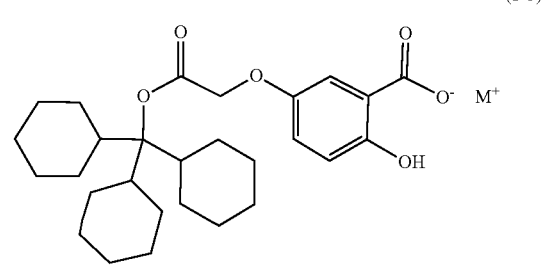

(1-3)

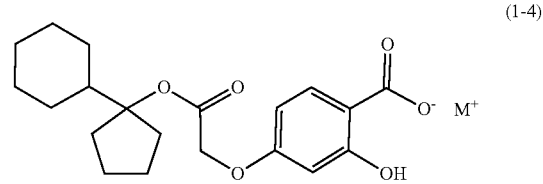

(1-4)

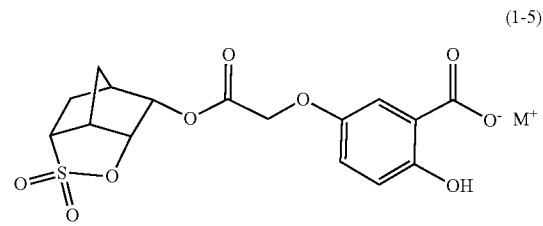

(1-5)

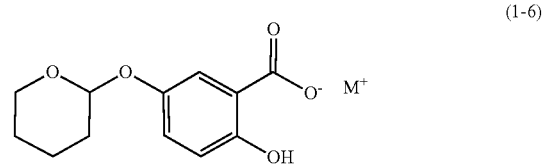

(1-6)

-continued (1-7) 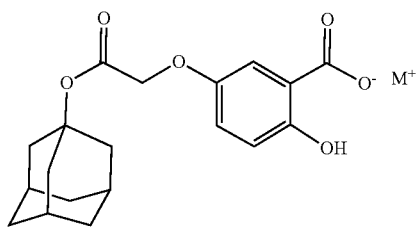

(1-8) 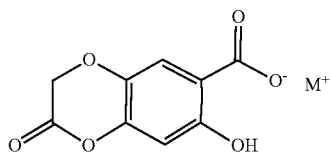

(1-9) 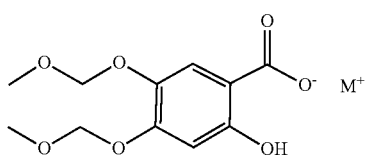

(1-10) 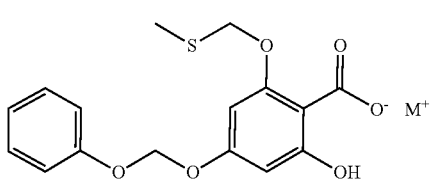

(1-11) 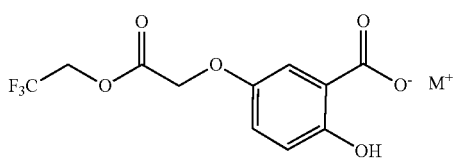

(1-12) 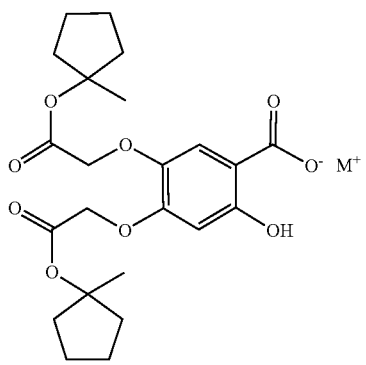

(1-13) 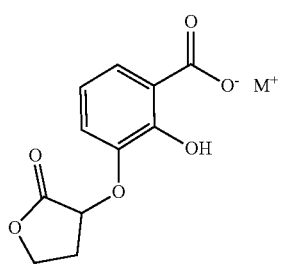

-continued (1-14)

(1-15)

(1-16)

(1-17)

(1-18)

In the above formulae (1-1) to (1-18), M$^+$ represents a monovalent radiation-sensitive onium cation.

The lower limit of a content of the compound (C) in the radiation-sensitive resin composition with respect to 100 parts by mass of the polymer (A) is preferably 0.1 parts by mass, and more preferably 1 part by mass. The upper limit of the content is preferably 20 parts by mass, more preferably 10 parts by mass, and still more preferably 20 parts by mass.

The lower limit of the content of the compound (C) in the radiation-sensitive resin composition with respect to 100 mol % of the acid generating agent (B) is preferably 1 mol %, more preferably 5 mol %, and still more preferably 10 mol %. The upper limit of the content is preferably 200 mol %, more preferably 100 mol %, and still more preferably 50 mol %.

When the content of the compound (C) falls within the above range, the sensitivity of the radiation-sensitive resin composition to exposure light, the LWR performance, and the CDU performance can be further improved. The radiation-sensitive resin composition may contain one, or two or more types of the compound (C).

For example, the compound (C) can be synthesized by a procedure indicated in the Examples, described later.

[c] Acid Diffusion Controller

The radiation-sensitive resin composition contains, as an optional component, the acid diffusion controller (c). The acid diffusion controller (c) is able to control a diffusion phenomenon of the acid generated from the acid generating agent (B) and the like upon exposure, thereby serving to inhibit unwanted chemical reactions in a non-exposed region. The acid diffusion controller (c) may be contained in the radiation-sensitive resin composition either in the form of a low-molecular-weight compound (hereinafter, may be also referred to as "(c) acid diffusion control agent" or "acid diffusion control agent (c)" as appropriate) or in a form in which it is incorporated as a part of a polymer such as the polymer (A), or may be in a combination of both these forms.

The acid diffusion control agent (c) is exemplified by a photodegradable base that is photosensitized by an exposure to generate a weak acid, and the like. Examples of the photodegradable base include: a compound containing a radiation-sensitive onium cation degraded by exposure, and an anion of a weak acid; and the like. As the photodegradable base generates, in a light-exposed region, a weak acid from a proton generated upon degradation of the radiation-sensitive onium cation and the anion of the weak acid, acid diffusion controllability decreases. Exemplary photodegradable bases include compounds represented by the following formulae.

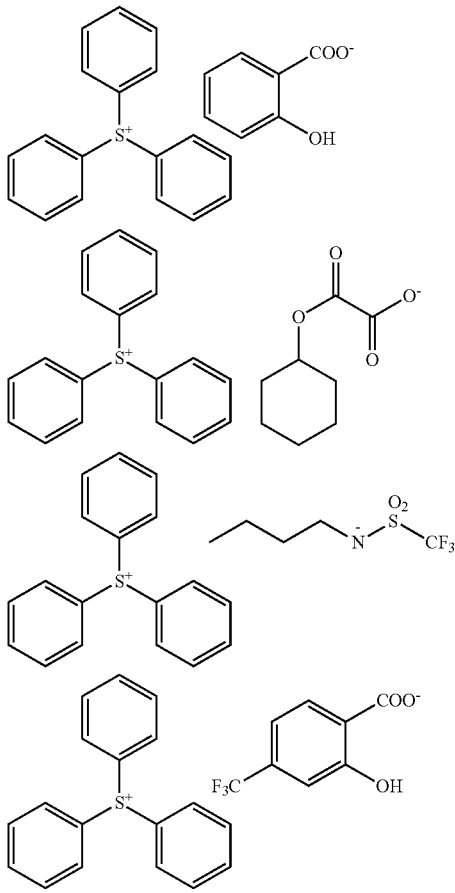

In the case in which the radiation-sensitive resin composition contains the acid diffusion control agent (c), the lower limit of a content of the acid diffusion control agent (c) with respect to 100 parts by mass of the polymer (A) is preferably 0.1 parts by mass, more preferably 0.5 parts by mass, and still more preferably 1 part by mass. The upper limit of the content is preferably 20 parts by mass, more preferably 10 parts by mass, and still more preferably 5 parts by mass.

The lower limit of the content of the acid diffusion control agent (c) with respect to 100 mol % of the acid generating agent (B) is preferably 1 mol %, more preferably 5 mol %, and still more preferably 10 mol %. The upper limit of the content is preferably 250 mol %, more preferably 150 mol %, and still more preferably 100 mol %.

When the content of the acid diffusion control agent (c) falls within the above range, the sensitivity of the radiation-sensitive resin composition to exposure light, the LWR performance, and the CDU performance can be further improved. The radiation-sensitive resin composition may contain one, or two or more types of the acid diffusion control agent (c).

(D) Solvent

The radiation-sensitive resin composition normally contains the solvent (D). The solvent (D) is not particularly limited as long as it is a solvent capable of dissolving or dispersing at least the polymer (A) and the compound (C), as well as the optional component(s) which is/are contained as desired.

The solvent (D) is exemplified by an alcohol solvent, an ether solvent, a ketone solvent, an amide solvent, an ester solvent, a hydrocarbon solvent, and the like.

Examples of the alcohol solvent include:

aliphatic monohydric alcohol solvents having 1 to 18 carbon atoms such as 4-methyl-2-pentanol;

alicyclic monohydric alcohol solvents having 3 to 18 carbon atoms such as cyclohexanol;

polyhydric alcohol solvents having 2 to 18 carbon atoms such as 1,2-propylene glycol;

polyhydric alcohol partial ether solvents having 3 to 19 carbon atoms such as propylene glycol-1-monomethyl ether; and the like.

Examples of the ether solvent include: dialkyl ether solvents such as diethyl ether; cyclic ether solvents such as tetrahydrofuran; aromatic ring-containing ether solvents such as diphenyl ether; and the like.

Examples of the ketone solvent include: chain ketone solvents such as acetone; cyclic ketone solvents such as cyclohexanone; 2,4-pentanedione, acetonylacetone, and acetophenone; and the like.

Examples of the amide solvent include cyclic amide solvents such as N,N'-dimethylimidazolidinone; chain amide solvents such as N-methylformamide; and the like.

Examples of the ester solvent include:

monocarboxylic acid ester solvents such as ethyl lactate;

polyhydric alcohol carboxylate solvents such as propylene glycol acetate;

polyhydric alcohol partial ether carboxylate solvents such as propylene glycol monomethyl ether acetate;

polyhydric carboxylic acid diester solvents such as diethyl oxalate;

lactone solvents such as γ-butyrolactone;

carbonate solvents such as dimethyl carbonate; and the like.

Examples of the hydrocarbon solvent include:

aliphatic hydrocarbon solvents having 5 to 12 carbon atoms such as n-pentane;

aromatic hydrocarbon solvents having 6 to 16 carbon atoms such as toluene; and the like.

Of these, the ester solvent and/or the ketone solvent are/is preferred; the polyhydric alcohol partial ether carboxylate solvent, the monocarboxylic acid ester solvent, the lactone solvent, and/or the cyclic ketone solvent are/is more preferred; and propylene glycol monomethyl ether acetate, ether lactate, γ-butyrolactone, and/or cyclohexanone are/is still more preferred. The radiation-sensitive resin composition may contain one, or two or more types of the solvent (D).

The lower limit of a proportion of the solvent (D) in the radiation-sensitive resin composition is preferably 50% by mass, more preferably 60% by mass, and still more preferably 70% by mass. The upper limit of the proportion is preferably 99.9 parts by mass, more preferably 99.5 parts by mass, and still more preferably 99 parts by mass.

The lower limit of the content of the solvent (D) with respect to 100 parts by mass of the polymer (A) is preferably 100 parts by mass, more preferably 500 parts by mass, and still more preferably 1,000 parts by mass. The upper limit of the content is preferably 20,000 parts by mass, more preferably 15,000 parts by mass, and still more preferably 10,000 parts by mass.

(E) Polymer

The polymer (E) is a polymer having a total percentage content by mass of fluorine atoms greater than that of the polymer (A). A polymer having greater hydrophobicity than another polymer serving as a base polymer tends to be localized in a surface layer of a resist film; thus, due to the polymer (E) having a total percentage content by mass of fluorine atoms and silicon atoms greater than that of the polymer (A), the polymer (E) tends to be localized in the surface layer of the resist film due to a characteristic arising from the hydrophobicity. Furthermore, due to the characteristic arising from the hydrophobicity, a receding contact angle of a liquid immersion medium on the resist film increases. Accordingly, due to including the polymer (E), the radiation-sensitive resin composition is particularly suited to liquid immersion lithography, and enables formation of a resist pattern whereby occurrence of defects is inhibited.

The lower limit of the total percentage content by mass of fluorine atoms and silicon atoms of the polymer (E) is preferably 1% by mass, more preferably 2% by mass, and still more preferably 3% by mass. The upper limit of the percentage content by mass is preferably 60% by mass, more preferably 50% by mass, and still more preferably 40% by mass. When the total percentage content by mass of fluorine atoms and silicon atoms falls within the above range, localization of the polymer (E) in the resist film can be more adequately adjusted. It is to be noted that the total percentage content by mass of fluorine atoms and silicon atoms in the polymer may be calculated by determining a structure of the polymer by $^{13}$C-NMR spectrometry, and calculating the content based on the structure thereof.

In the case of including the fluorine atom in the polymer (E), the mode of incorporation of the fluorine atom in the polymer (E) is not particularly limited, and the fluorine atom may bond to any of a main chain, a side chain, and an end of the polymer (E); however, the polymer (E) preferably has a structural unit (hereinafter, may be also referred to as "structural unit "F") that includes a fluorine atom.

Structural Unit (F)

Examples of the structural unit (F) include a structural unit represented by the following formula (f-1) (hereinafter, may be also referred to as "structural unit (f-1)"), and the like.

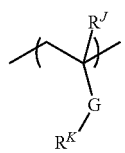

(f-1)

In the above formula (f-1), $R^J$ represents a hydrogen atom, a fluorine atom, a methyl group or a trifluoromethyl group; G represents a single bond, an oxygen atom, a sulfur atom, —COO—, —SO$_2$NH—, —CONH— or —OCONH—; and $R^K$ represents a monovalent organic group having 1 to 18 carbon atoms and including a fluorine atom.

In light of a degree of copolymerization of a monomer that gives the structural unit (f-1), $R^J$ represents preferably a hydrogen atom or a methyl group, and more preferably a methyl group. G represents preferably —COO—, —SO$_2$NH—, —CONH—, or —OCONH—, and more preferably —COO—.

The lower limit of a proportion of the structural unit (F) contained with respect to total structural units constituting the polymer (E) is preferably 10 mol %, more preferably 20 mol %, and still more preferably 30 mol %. The upper limit of the proportion is preferably 100 mol %, more preferably 90 mol %, and still more preferably 85 mol %. When the proportion of the polymer (F) falls within the above range, the percentage content by mass of fluorine atoms in the polymer (E) can be more appropriately adjusted.

The polymer (E) preferably has a structural unit that includes an alcoholic hydroxyl group. Examples of the structural unit that includes an alcoholic hydroxyl group include structural units exemplified as the structural unit (III) in the polymer (A), and the like. The lower limit of a proportion of the structural unit that includes the alcoholic hydroxyl group contained with respect to total structural units constituting the polymer (E) is preferably 10 mol %, more preferably 15 mol %, and still more preferably 20 mol %. The upper limit of the proportion is preferably 90 mol %, more preferably 85 mol %, and still more preferably 70 mol %.

The lower limit of the content of the solvent (E) with respect to 100 parts by mass of the polymer (A) is preferably 0.1 parts by mass, more preferably 1 part by mass, and still more preferably 2 parts by mass. The upper limit of the content is preferably 20 parts by mass, more preferably 10 parts by mass, and still more preferably 7.5 parts by mass. The radiation-sensitive resin composition may contain one, or two or more types of the polymer (E).

The polymer (E) can be synthesized by a procedure similar to that for the polymer (A), mentioned above.

The lower limit of the Mw of the polymer (E) as determined by GPC is preferably 1,000, more preferably 3,000, still more preferably 4,000, and particularly preferably 5,000. The upper limit of the Mw is preferably 50,000, more preferably 20,000, still more preferably 10,000, and particularly preferably 8,000.

The upper limit of a ratio (Mw/Mn) of the Mw to the Mn of the polymer (E) as determined by GPC is preferably 5.00, more preferably 3.00, still more preferably 2.50, and particularly preferably 2.00. The lower limit of the ratio is generally 1.00, and preferably 1.20.

Other Optional Component(s)

The other optional component(s) is/are exemplified by a surfactant and the like. The radiation-sensitive resin composition may contain one, or two or more types each of the other optional component(s).

Preparation Procedure of Radiation-Sensitive Resin Composition

The radiation-sensitive resin composition may be prepared, for example, by mixing the polymer (A) and the compound (C), as well as the optional component(s) such as the acid generating agent (B), the acid diffusion controller (c), or/and the polymer (E) which is/are added as needed, in a certain ratio, and preferably filtering a thus resulting mixture through a membrane filter having a pore size of no greater than 0.2 μm.

The radiation-sensitive resin composition may be used for either positive-tone pattern formation conducted using an alkaline developer solution, or negative-tone pattern formation conducted using an organic solvent-containing developer solution. The radiation-sensitive resin composition may be suitably used for any of ArF exposure involving exposure to an ArF excimer laser beam, EUV exposure involving exposure to an extreme ultraviolet ray (EUV), or electron beam exposure involving exposure to an electron beam.

Resist Pattern-Forming Method

The resist pattern-forming method according to an embodiment of the present invention includes: a step of applying the radiation-sensitive resin composition according to the embodiment of the invention directly or indirectly on a substrate (hereinafter, may be also referred to as "applying step"); a step of exposing the resist film formed by the applying step (hereinafter, may be also referred to as "exposing step"); and a step of developing the resist film exposed (hereinafter, may be also referred to as "developing step").

According to the resist pattern-forming method, due to use of the radiation-sensitive resin composition, formation of a resist pattern having favorable sensitivity to exposure light, as well as low LWR and low CDU, is enabled. Hereinafter, each step will be described.

Applying Step

In this step, the radiation-sensitive resin composition according to the first embodiment of the invention is applied directly or indirectly on a substrate to thereby form a resist film. The substrate is exemplified by a conventionally well-known substrate such as a silicon wafer, a wafer coated with silicon dioxide or aluminum, and the like. In addition, an organic or inorganic antireflective film disclosed in, for example, Japanese Examined Patent Application, Publication No. H6-12452, Japanese Unexamined Patent Application, Publication No. S59-93448, or the like may be provided on the substrate. An application procedure is exemplified by spin-coating, cast coating, roll-coating, and the like. After the applying, prebaking (PB) may be carried out as needed to evaporate the solvent remaining in the coating film. The lower limit of a temperature of the PB is preferably 60° C., and more preferably 80° C. The upper limit of the temperature of the PB temperature is preferably 150° C., and more preferably 140° C. The lower limit of a time period of the PB is preferably 5 sec, and more preferably 10 sec. The upper limit of the time period of the PB is preferably 600 sec, and more preferably 300 sec. The lower limit of an average thickness of the resist film formed is preferably 10 nm, and more preferably 20 nm. The upper limit of the average thickness is preferably 1,000 nm, and more preferably 500 nm.

Exposing Step

In this step, the resist film formed by the applying step is exposed. This exposure is carried out by irradiation with an exposure light through a photomask (as the case may be, through a liquid immersion medium such as water). Examples of the exposure light include: electromagnetic waves such as visible light rays, ultraviolet rays, far ultraviolet rays, EUV, X-rays, and γ-rays; charged particle rays such as electron beams and α-rays; and the like, which may be selected in accordance with a line width and the like of the intended pattern. Of these, far ultraviolet rays, EUV, or electron beams are preferred; an ArF excimer laser beam (wavelength: 193 nm), a KrF excimer laser beam (wavelength: 248 nm), EUV, or an electron beam is more preferred; and an ArF excimer laser beam or EUV is still more preferred. It is to be noted that exposure conditions such as exposure dose and the like can be appropriately selected in accordance with a formulation of the radiation-sensitive resin composition, type(s) of additive(s), a type of exposure light, and the like.

It is preferred that post exposure baking (PEB) is carried out after the exposure to promote dissociation of the acid-labile group included in the polymer (A) by the acid generated upon the exposure in exposed regions of the resist film. This PEB enables an increase in a difference in solubility in a developer solution between the light-exposed regions and light-unexposed regions. The lower limit of a temperature of the PEB is preferably 50° C., more preferably 80° C., and still more preferably 90° C. The upper limit of the temperature is preferably 180° C., and more preferably 130° C. The lower limit of a time period of the PEB is preferably 5 sec, more preferably 10 sec, and still more preferably 30 sec. The upper limit of the time period is preferably 600 sec, more preferably 300 sec, and still more preferably 100 sec.

Developing Step

In this step, the resist film exposed is developed. Accordingly, formation of a predetermined resist pattern is enabled. After the development, washing with a rinse agent such as water or an alcohol and then drying is typical. The development procedure in the developing step may be either development with an alkali, in which an alkaline developer solution is used; or development with an organic solvent, in which a developer solution containing an organic solvent is used.

In the case of the development with an alkali, the alkaline developer solution for use in the development is exemplified by alkaline aqueous solutions prepared by dissolving at least one alkaline compound such as sodium hydroxide, sodium carbonate, sodium silicate, sodium metasilicate, aqueous ammonia, ethylamine, n-propylamine, diethylamine, di-n-propylamine, trimethylamine, methyldiethylamine, ethyldiethylamine, triethanolamine, tetramethylammonium hydroxide (TMAH), pyrrole, piperidine, choline, 1,8-diazabicyclo-[5.4.0]-7-undecene, 1,5-diazabicyclo-[4.3.0]-5-nonene, etc., and the like. Of these, an aqueous TMAH solution is preferred, and a 2.38% by mass aqueous TMAH solution is more preferred.

In the case of the development with an organic solvent, the developer solution containing the organic solvent is exemplified by: an organic solvent such as an alcohol solvent, an ether solvent, a ketone solvent, an ester solvent, and a hydrocarbon solvent; a solvent containing the organic solvent; and the like. An exemplary organic solvent includes one, or two or more types of the solvents exemplified as the solvent (D), and the like. Of these, the ester solvent or the ketone solvent is preferred. The ester solvent is preferably an acetic acid ester solvent, and more preferably n-butyl acetate. The ketone solvent is preferably a chain ketone, and more preferably 2-heptanone. The lower limit of the content of the organic solvent in the developer solution is preferably 80% by mass, more preferably 90% by mass, still more preferably 95% by mass, and particularly preferably 99% by mass. Components other than the organic solvent in the developer solution are exemplified by water, silicon oil, and the like.

Examples of the development procedure include: a dipping procedure in which the substrate is immersed for a given time period in the developer solution charged in a container; a puddle procedure in which the developer solution is placed to form a dome-shaped bead by way of the surface tension on the surface of the substrate for a given time period to conduct a development; a spraying procedure in which the developer solution is sprayed onto the surface of the substrate; a dynamic dispensing procedure in which the developer solution is continuously applied onto the substrate, which is rotated at a constant speed, while scanning with a developer solution-application nozzle at a constant speed; and the like.

The resist pattern to be formed according to the resist pattern-forming method is exemplified by a line-and-space pattern, a hole pattern, and the like.

Acid Diffusion Control Agent

The acid diffusion control agent of an embodiment of the present invention is the compound (C) which is represented by the above formula (1). The acid diffusion control agent can be suitably used as a component of the radiation-sensitive resin composition of the embodiment of the present invention described above. The acid diffusion control agent is described above as the compound (C).

Compound

The compound of an embodiment of the present invention is the compound (C) which is represented by the above formula (1). The compound can be suitably used as a component of the radiation-sensitive resin composition of the embodiment of the present invention described above. The compound is described above as the compound (C).

EXAMPLES

Hereinafter, the present invention is explained in detail by way of Examples, but the present invention is not in any way limited to these Examples. Measuring methods for various types of physical properties are shown below.

Measurements of Weight Average Molecular Weight (Mw) and Number Average Molecular Weight (Mn)

Measurements of the Mw and the Mn of the polymer were carried out by gel permeation chromatography (GPC) using GPC columns available from Tosoh Corporation ("G2000 HXL"×2, "G3000 HXL"×1 and "G4000 HXL"×1) under the following analytical conditions. Furthermore a dispersity index (Mw/Mn) was calculated according to measurement results of the Mw and the Mn.

elution solvent: tetrahydrofuran
flow rate: 1.0 mL/min
sample concentration: 1.0% by mass
amount of injected sample: 100 μL
column temperature: 40° C.
detector: differential refractometer
standard substance: mono-dispersed polystyrene $^{13}$C-NMR Analysis $^{13}$C-NMR analysis of the polymer was carried out by using a nuclear magnetic resonance apparatus ("JNM-Delta400," available from JEOL, Ltd.).

Synthesis of (A) Polymer and (E) Polymer

Monomers used for synthesizing the polymers in the Examples and Comparative Examples are presented below. It is to be noted that in the following Synthesis Examples, unless otherwise specified particularly, "parts by mass" means a value, provided that the total mass of the monomers used was 100 parts by mass, and "mol %" means a value, provided that the total mol number of the monomers used was 100 mol %.

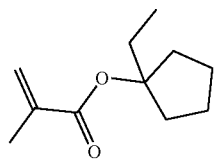
(M-1)

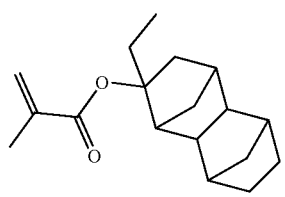
(M-2)

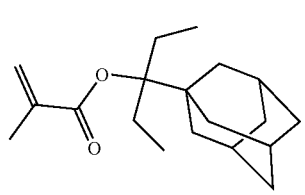
(M-3)

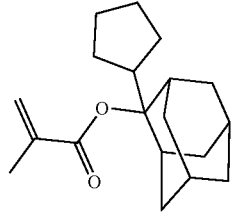
(M-4)

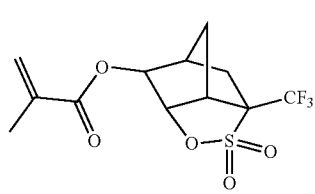
(M-5)

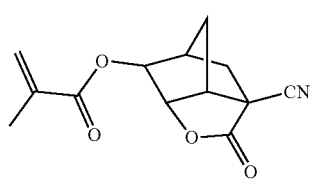
(M-6)

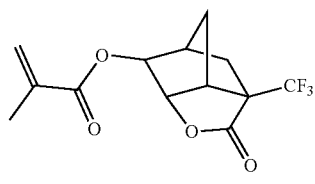
(M-7)

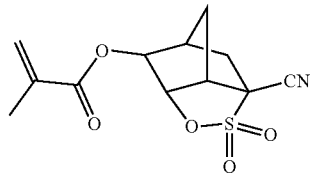
(M-8)

-continued (M-9) 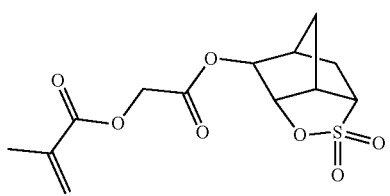

(M-10) 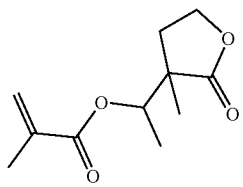

(M-11) 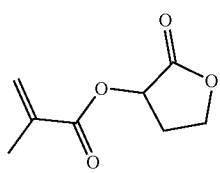

(M-12) 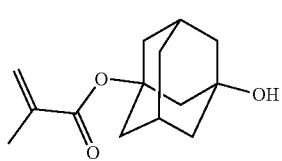

(M-13) 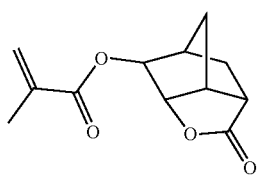

(M-14) 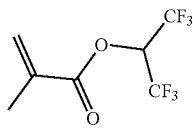

(M-15) 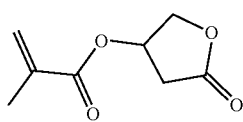

(M-16) 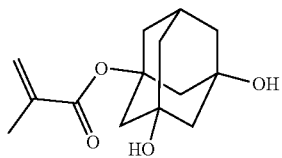

(M-17) 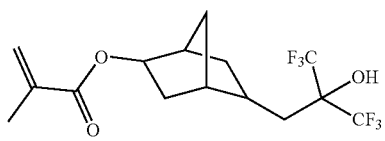

(M-18) 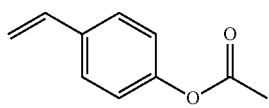

(M-19) 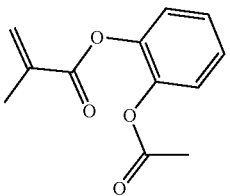

(M-20) 

(M-21) 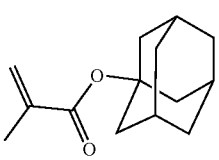

(M-22) 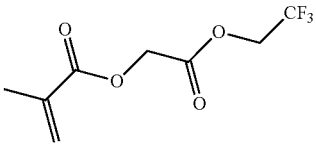

Synthesis Example 1: Synthesis of Polymer (A-1)

The monomer (M-1), the monomer (M-2), and the monomer (M-10) were dissolved in 2-butanone (200 parts by mass) such that the molar ratio became 40/15/45 (mol %), and a monomer solution was prepared by adding to this solution AIBN (azobisisobutyronitrile) as an initiator (2 mol % with respect to a total of 100 mol % of the monomers used). Into a reaction vessel was placed 2-butanone (100 parts by mass), purging with nitrogen was conducted for 30 min, the internal temperature of the reaction vessel was adjusted to 80° C., and the monomer solution prepared as described above was added dropwise thereto over 3 hrs with stirring. Onset of the dropwise addition was regarded as the time point of the start of the polymerization reaction, and the polymerization reaction was performed for 6 hrs. After completion of the polymerization reaction, the polymerization solution was water-cooled to 30° C. or below. The cooled polymerization solution was charged into methanol (2,000 parts by mass), and a thus precipitated white powder was filtered off. The white powder obtained by filtration was washed twice with methanol, followed by filtering off and drying at 50° C. for 17 hrs to give a white powdery polymer (A-1) (yield: 80%). The Mw of the polymer (A-1) was 8,700, and the Mw/Mn was 1.49. Furthermore, as a result of the $^{13}$C-NMR analysis, the proportions of the structural units derived from (M-1), (M-2), and (M-10) were, respectively, 39.9 mol %, 14.3 mol %, and 45.8 mol %.

Synthesis Examples 2 to 11: Synthesis of Polymer (A-2) to Polymer (A-11)

Polymers (A-2) to (A-11) were obtained by a similar operation to that of Synthesis Example 1, except that each monomer of the type and in the blend proportion shown in Table 1 below was used. The proportion (mol %) and the yield (%) of each structural unit, and the physical properties (the Mw and the Mw/Mn) of each polymer thus obtained are shown together in Table 1 below. It is to be noted that in Table 1, "–" indicates that the corresponding monomer was not used.

TABLE 1

| (A) Polymer | Monomer that gives structural unit (I) type | proportion (mol %) | proportion of structural unit (mol %) | Monomer that gives structural unit (II) Type | proportion (mol %) | proportion of structural unit (mol %) | Monomer that gives structural unit (III) Type | proportion (mol %) | proportion of structural unit (mol %) | Mw | Mw/Mn |
|---|---|---|---|---|---|---|---|---|---|---|---|
| Synthesis Example 1 | A-1 | M-1 40 | 39.9 | M-10 | 45 | 45.8 | — | — | — | 8,700 | 1.49 |
| | | M-2 15 | 14.3 | | | | | | | | |
| Synthesis Example 2 | A-2 | M-1 30 | 31.4 | M-15 | 60 | 60.6 | — | — | — | 9,000 | 1.44 |
| | | M-2 10 | 8.0 | | | | | | | | |
| Synthesis Example 3 | A-3 | M-1 30 | 31.9 | M-11 | 60 | 61.7 | — | — | — | 8,900 | 1.39 |
| | | M-3 10 | 6.4 | | | | | | | | |
| Synthesis Example 4 | A-4 | M-1 35 | 32.3 | M-13 | 45 | 49.6 | — | — | — | 8,500 | 1.59 |
| | | M-3 20 | 18.1 | | | | | | | | |
| Synthesis Example 5 | A-5 | M-1 40 | 41.1 | M-9 | 45 | 45.7 | — | — | — | 8,700 | 1.44 |
| | | M-4 15 | 13.2 | | | | | | | | |
| Synthesis Example 6 | A-6 | M-1 40 | 41.6 | M-8 | 45 | 46.1 | — | — | — | 7,700 | 1.51 |
| | | M-4 15 | 12.3 | | | | | | | | |
| Synthesis Example 7 | A-7 | M-1 40 | 42.4 | M-7 | 45 | 39.5 | M-12 | 15 | 18.1 | 7,800 | 1.59 |
| Synthesis Example 8 | A-8 | M-1 40 | 41.1 | M-6 | 40 | 35.7 | M-16 | 20 | 23.2 | 8,100 | 1.56 |
| Synthesis Example 9 | A-9 | M-1 50 | 49.8 | M-5 | 40 | 43.0 | — | — | — | 8,200 | 1.60 |
| | | M-4 10 | 7.2 | | | | | | | | |
| Synthesis Example 10 | A-10 | M-1 40 | 44.4 | M-13 | 60 | 55.6 | — | — | — | 7,900 | 1.59 |
| Synthesis Example 11 | A-11 | M-1 40 | 42.8 | M-6 | 60 | 57.2 | — | — | — | 8,000 | 1.43 |

Synthesis Example 12: Synthesis of Polymer (A-12)

The monomer (M-3), the monomer (M-18), and the monomer (M-12) were dissolved in 1-methoxy-2-propanol (200 parts by mass) such that the molar ratio became 60/30/10 (mol %), and a monomer solution was prepared by adding to this solution AIBN as an initiator (5 mol %). Into a reaction vessel was placed 1-methoxy-2-propanol (100 parts by mass), purging with nitrogen was conducted for 30 min, the internal temperature of the reaction vessel was adjusted to 80° C., and the monomer solution prepared as described above was added dropwise thereto over 3 hrs with stirring. Onset of the dropwise addition was regarded as the time point of the start of the polymerization reaction, and the polymerization reaction was performed for 6 hrs. After completion of the polymerization reaction, the polymerization solution was water-cooled to 30° C. or below. The cooled polymerization solution was charged into hexane (2,000 parts by mass), and a thus precipitated white powder was filtered off. The white powder obtained by filtration was washed twice with hexane, followed by filtering off and dissolution in 1-methoxy-2-propanol (300 parts by mass). Next, methanol (500 parts by mass), trimethylamine (50 parts by mass), and ultra-pure water (10 parts by mass) were added to a resulting solution, and a hydrolysis reaction was performed at 70° C. for 6 hrs with stirring. After completion of the reaction, the remaining solvent was distilled away and the solid thus obtained was dissolved in acetone (100 parts by mass) and a resulting solution was added dropwise into water (500 parts by mass) to permit coagulation of the resin. A solid thus obtained was filtered off, and drying at 50° C. for 13 hrs gave a white powdery polymer (A-12) (yield: 78%). The Mw of the polymer (A-12) was 5,500, and the Mw/Mn was 1.55. Furthermore, as a result of the $^{13}$C-NMR analysis, the proportions of the structural units derived from (M-3), (M-18), and (M-12) were, respectively, 59.4 mol %, 32.1 mol %, and 8.5 mol %.

Synthesis Examples 13 to 15: Synthesis of Polymer (A-13) to Polymer (A-15)

Polymers (A-13) to (A-15) were obtained by a similar operation to that of Synthesis Example 12, except that each monomer of the type and in the blend proportion shown in Table 2 below was used. The proportion (mol %) and the yield (%) of each structural unit, and the physical properties (the Mw and the Mw/Mn) of each polymer thus obtained are shown together in Table 2 below.

TABLE 2

| (A) Polymer | Monomer that gives structural unit (I) type | blend proportion (mol %) | proportion of structural unit (mol %) | Monomer that gives structural unit (III) type | blend proportion (mol %) | proportion of structural unit (mol %) | Monomer that gives structural unit (IV) type | blend proportion (mol %) | proportion of structural unit (mol %) | Mw | Mw/Mn |
|---|---|---|---|---|---|---|---|---|---|---|---|
| Synthesis Example 12 | A-12 | M-3 | 60 | 59.4 | M-12 | 10 | 8.5 | M-18 | 30 | 32.1 | 5,500 | 1.55 |
| Synthesis Example 13 | A-13 | M-3 | 50 | 47.7 | M-16 | 20 | 20.1 | M-19 | 30 | 32.2 | 5,800 | 1.51 |

TABLE 2-continued

| (A) Polymer | Monomer that gives structural unit (I) | | | Monomer that gives structural unit (III) | | | Monomer that gives structural unit (IV) | | | Mw | Mw/Mn |
|---|---|---|---|---|---|---|---|---|---|---|---|
| | type | blend proportion (mol %) | proportion of structural unit (mol %) | type | blend proportion (mol %) | proportion of structural unit (mol %) | type | blend proportion (mol %) | proportion of structural unit (mol %) | | |
| Synthesis Example 14 | A-14 | M-2 | 50 | 48.1 | M-17 | 20 | 21.3 | M-18 | 30 | 30.6 | 5,100 | 1.59 |
| Synthesis Example 15 | A-15 | M-2 | 55 | 54.3 | M-17 | 15 | 15.6 | M-19 | 30 | 30.1 | 5,000 | 1.41 |

Synthesis Example 16: Synthesis of Polymer (E-1)

The monomer (M-1) and the monomer (M-20) were dissolved in 2-butanone (200 parts by mass) such that the molar ratio became 20/80 (mol %), and a monomer solution was prepared by adding to this solution AIBN as an initiator (3 mol %). Into a reaction vessel was placed 2-butanone (100 parts by mass), purging with nitrogen was conducted for 30 min, the internal temperature of the reaction vessel was adjusted to 80° C., and the monomer solution prepared as described above was added dropwise thereto over 3 hrs with stirring. Onset of the dropwise addition was regarded as the time point of the start of the polymerization reaction, and the polymerization reaction was performed for 6 hrs. After completion of the polymerization reaction, the polymerization solution was water-cooled to 30° C. or below. After the solvent was replaced with acetonitrile (400 parts by mass), an operation including: adding hexane (100 parts by mass); stirring the mixture; and collecting the acetonitrile layer was repeated three times. The solvent was replaced with propylene glycol monomethyl ether acetate to give a solution of a polymer (E-1) (yield: 69%). The Mw of the polymer (E-1) was 6,000, and the Mw/Mn was 1.62. Furthermore, as a result of the $^{13}$C-NMR analysis, the proportions of the structural units derived from (M-1) and (M-20) were, respectively, 19.9 mol % and 80.1 mol %.

Synthesis Examples 17 to 20: Synthesis of Polymer (E-2) to Polymer (E-5)

Polymers (E-2) to (E-5) were obtained by a similar operation to that of Synthesis Example 16, except that each monomer of the type and in the blend proportion shown in Table 3 below was used. The proportion (mol %) and the yield (%) of each structural unit, and the physical properties (the Mw and the Mw/Mn) of each polymer thus obtained are shown together in Table 3.

TABLE 3

| | (E) Polymer | Monomer that gives structural unit (F) | | | Monomer that gives structural unit (I) | | | Monomer that gives structural unit (III) type |
|---|---|---|---|---|---|---|---|---|
| | | type | blend proportion (mol %) | proportion of structural unit (mol %) | type | blend proportion (mol %) | proportion of structural unit (mol %) | |
| Synthesis Example 16 | E-1 | M-20 | 80 | 80.1 | M-1 | 20 | 19.9 | — |
| Synthesis Example 17 | E-2 | M-22 | 80 | 81.9 | M-1 | 20 | 18.1 | — |
| Synthesis Example 18 | E-3 | M-14 | 60 | 62.3 | — | — | — | — |
| Synthesis Example 19 | E-4 | M-14 | 70 | 68.7 | — | — | — | M-12 |
| Synthesis Example 20 | E-5 | M-14 | 70 | 72.3 | — | — | — | M-17 |

| | Monomer that gives structural unit (III) | | Monomer that gives other structural unit(s) | | | Mw | Mw/Mn |
|---|---|---|---|---|---|---|---|
| | blend proportion (mol %) | proportion of structural unit (mol %) | type | blend proportion (mol %) | proportion of structural unit (mol %) | | |
| Synthesis Example 16 | — | — | — | — | — | 6,000 | 1.62 |
| Synthesis Example 17 | — | — | — | — | — | 7,200 | 1.77 |
| Synthesis Example 18 | — | — | M-21 | 40 | 37.7 | 6,300 | 1.82 |
| Synthesis Example 19 | 30 | 31.3 | — | — | — | 6,500 | 1.81 |
| Synthesis Example 20 | 30 | 27.7 | — | — | — | 6,200 | 1.78 |

Synthesis of (C) Compound (Acid Diffusion Control Agent)

Synthesis Example 21: Synthesis of Compound (C-1)

Into a reaction vessel were added 20.0 mmol of methyl 2,5-dihydroxybenzoate, 30.0 mmol of 1-ethylcyclopentyl-2-chloroacetate, 40.0 mmol of cesium carbonate, and 50 g of dimethylformamide, followed by stirring at 80° C. for 5 hrs. Thereafter, the reaction solution was cooled to 30° C. or below, and after diluting with water, ethyl acetate was added to conduct extraction, and the organic layer was separated. The organic layer thus obtained was washed with a saturated aqueous sodium chloride solution, and then water. After drying over sodium sulfate, the solvent was distilled away, and then purification by column chromatography gave a phenol derivative with a favorable yield.

After a mixture of methanol: water (1:1 (mass ratio)) was added to the phenol derivative to give a 1 M solution, 18.5 mmol of sodium hydroxide was added thereto, and a reaction was allowed at 50° C. for 4 hrs. Extraction was conducted with acetonitrile and the solvent was distilled away to give a sodium salt derivative. To the sodium salt derivative was added 15.0 mmol of triphenylsulfonium chloride, and then a mixture of water: dichloromethane (1:3 (mass ratio)) was added thereto. After the mixture was vigorously stirred at room temperature for 3 hrs, dichloromethane was added to conduct extraction, and the organic layer was separated. The organic layer thus obtained was dried over sodium sulfate and the solvent was distilled away to give a compound represented by the following formula (C-1) (hereinafter, may be also referred to as "compound (C-1)" or "acid diffusion control agent (C-1)") with a favorable yield. A synthesis scheme of the compound (C-1) is shown below.

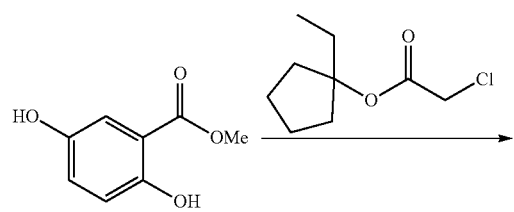

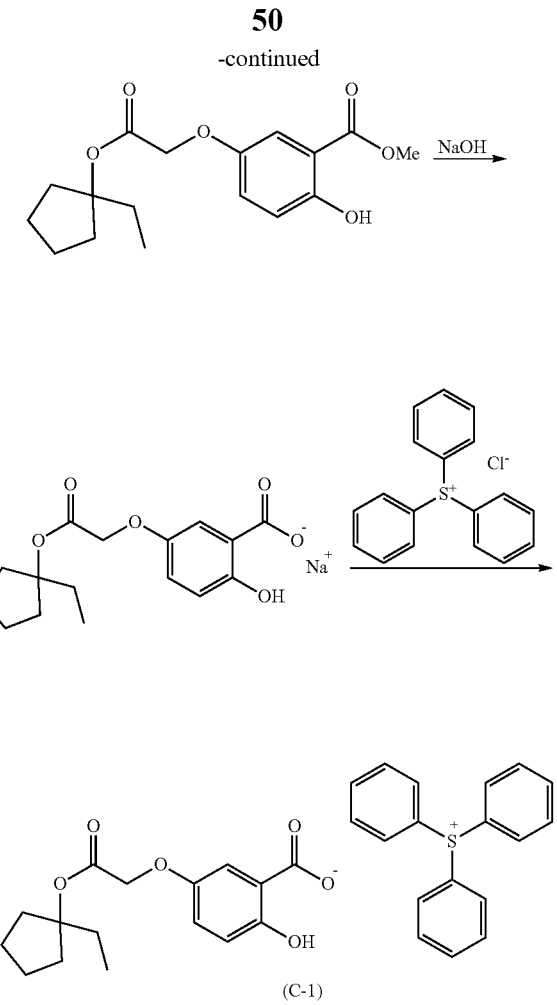

Synthesis Examples 22 to 38: Synthesis of Acid Diffusion Control Agent (C-2) to Acid Diffusion Control Agent (C-18)

Compounds represented by the following formulae (C-2) to (C-18) were obtained by a similar operation to that of Synthesis Example 21, except that each source material and precursor was changed as appropriate (hereinafter, the compounds represented by the following formulae (C-2) to (C-18) may be referred to as, respectively, "compound (C-2)" to "compound (C-18)," or "acid diffusion control agent (C-2)" to "acid diffusion control agent (C-18)").

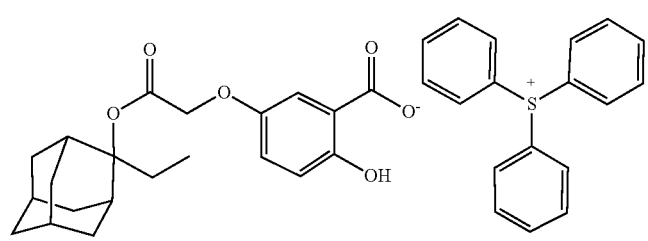

(C-2)

-continued
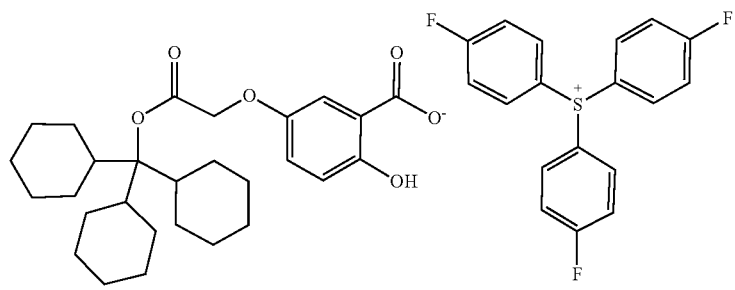
(C-3)
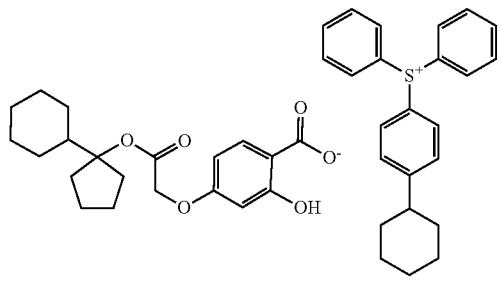
(C-4)
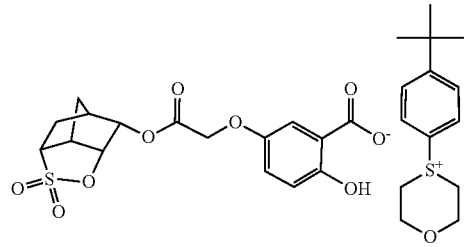
(C-5)
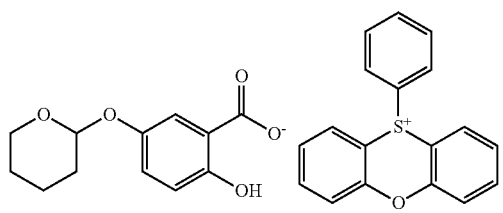
(C-6)
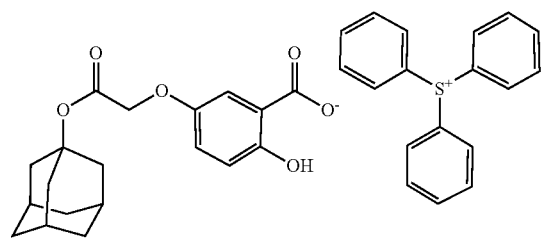
(C-7)
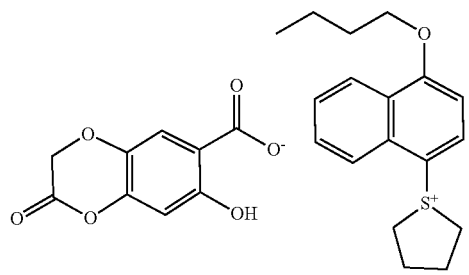
(C-8)
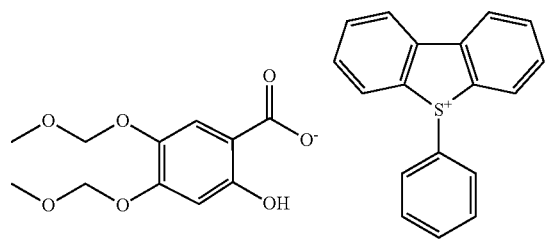
(C-9)
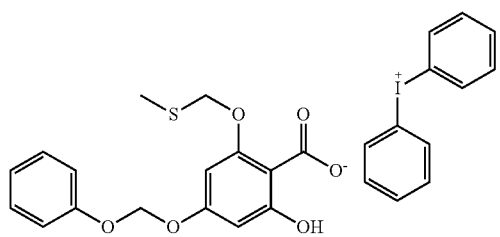
(C-10)
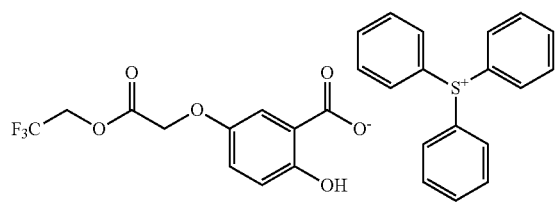
(C-11)

-continued
(C-12) 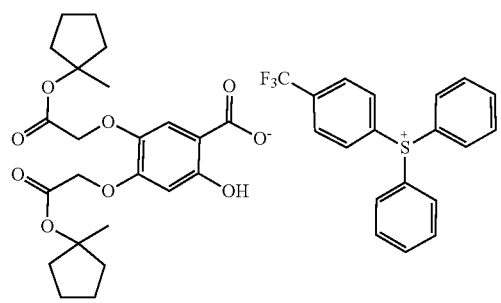
(C-13) 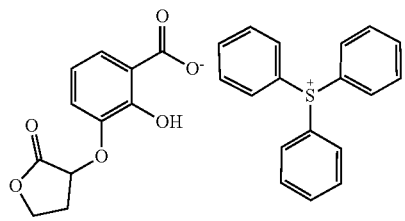
(C-14) 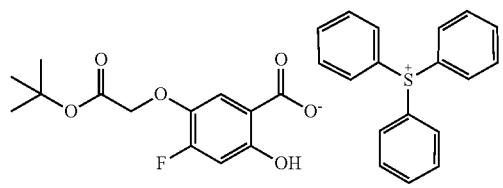
(C-15) 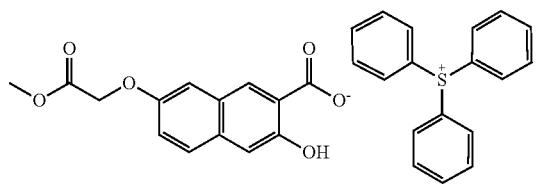
(C-16) 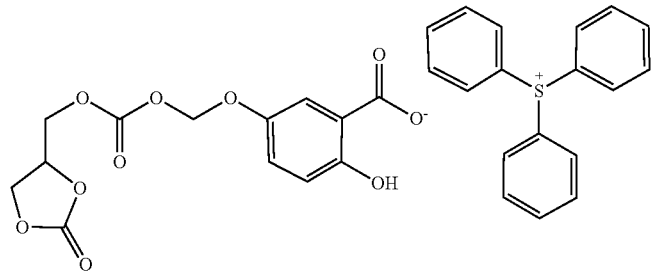
(C-17) 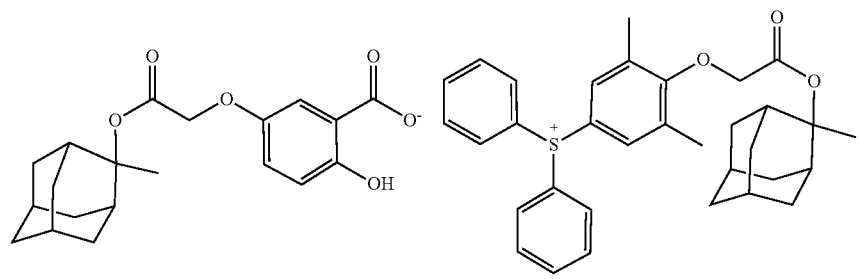
(C-18) 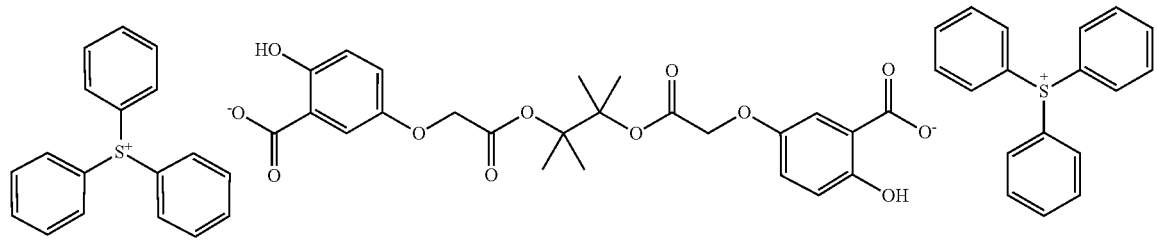

Preparation of Radiation-Sensitive Resin Composition
Components other than the polymer (A), the polymer (E), and the acid diffusion control agent (C) used for preparing the radiation-sensitive resin compositions are shown below.
(B) Acid Generating Agent
B-1 to B-16: compounds represented by the following formulae (B-1) to (B-16)
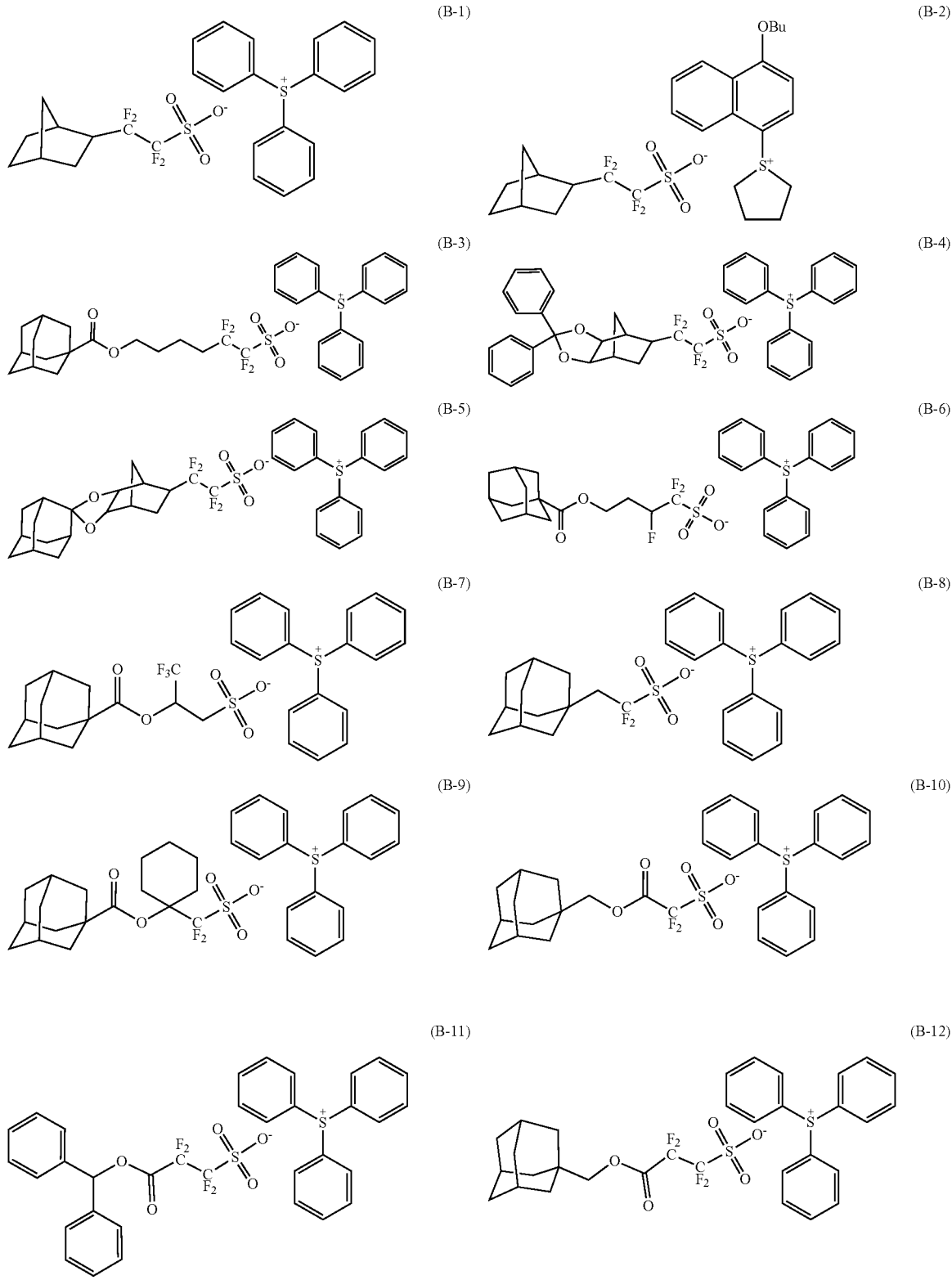

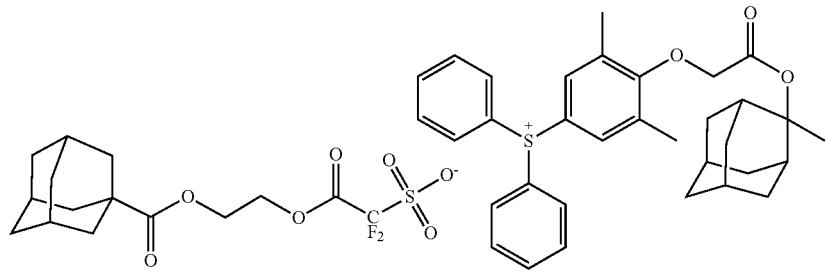
(B-13)
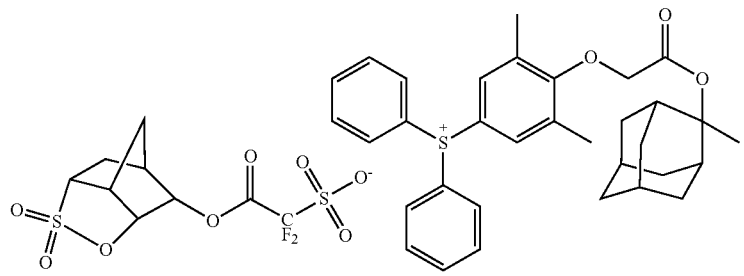
(B-14)
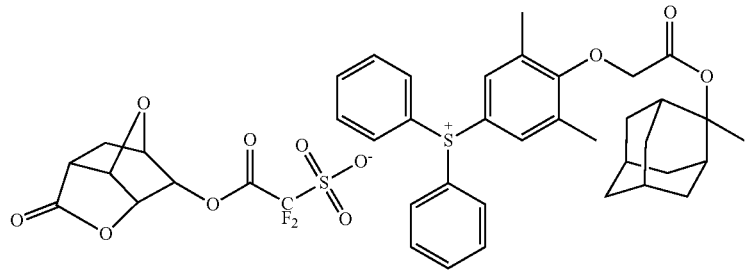
(B-15)
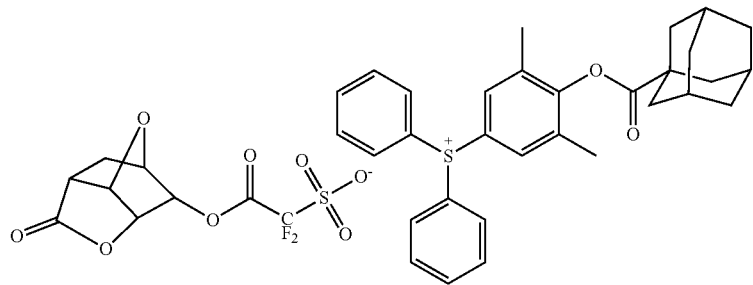
(B-16)

(c) Acid Diffusion Control Agents Other than Acid Diffusion Control Agents (C-1) to (C-18)

cc-1 to cc-9: compounds represented by the following formulae (cc-1) to (cc-9) (hereinafter, the compounds represented by the following formulae (cc-1) to (cc-9) may be referred to as, respectively, "compound (cc-1)" to "compound (cc-9)," or "acid diffusion control agent (cc-1)" to "acid diffusion control agent (cc-9)").

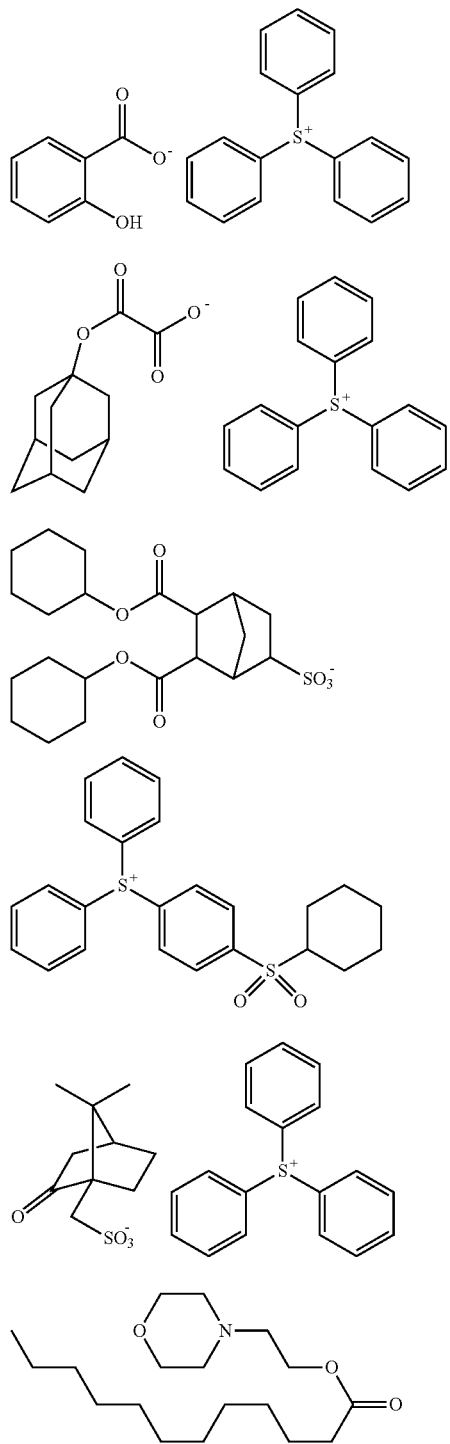

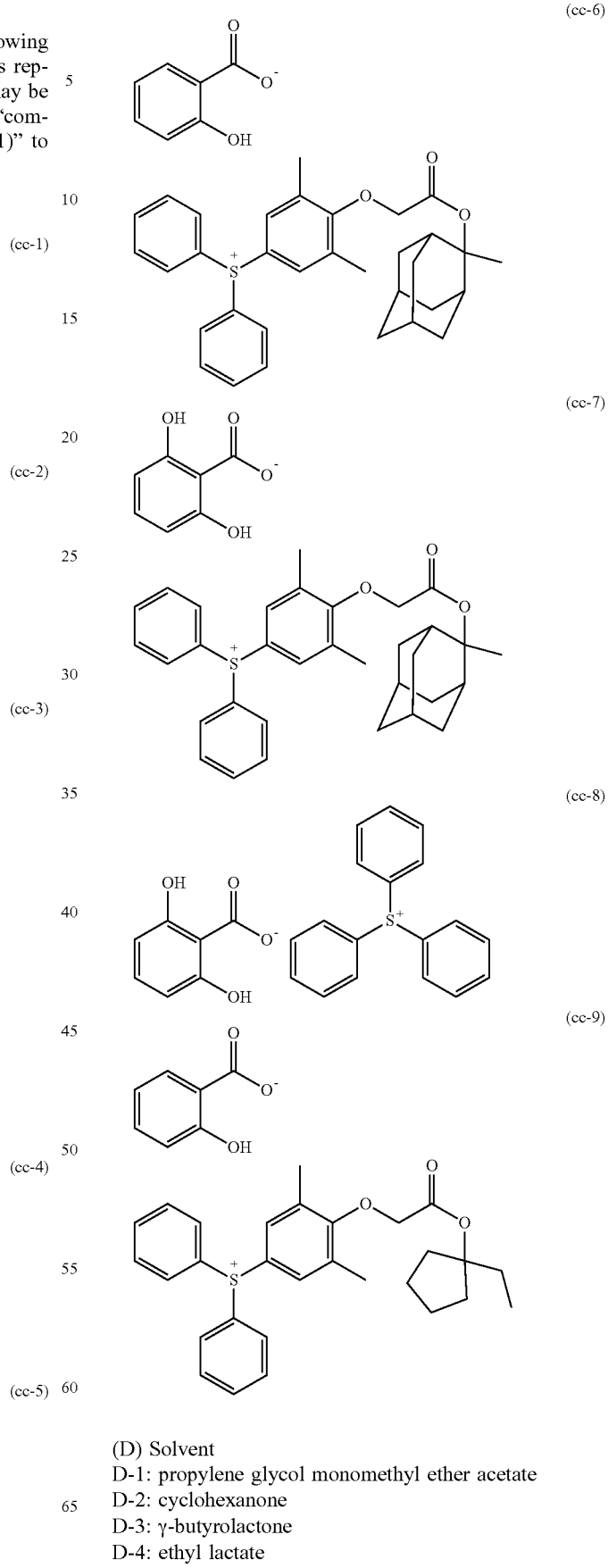

(D) Solvent
D-1: propylene glycol monomethyl ether acetate
D-2: cyclohexanone
D-3: γ-butyrolactone
D-4: ethyl lactate Preparation of Negative-Tone Radiation-Sensitive Resin Composition for ArF Exposure

Example 1

A radiation-sensitive resin composition (J-1) was prepared by: mixing 100 parts by mass of (A-1) as the polymer (A), 14.0 parts by mass of (B-5) as the acid generating agent (B), 2.3 parts by mass of (C-1) as the acid diffusion control agent (C), 5.0 parts by mass (solid content) of (E-1) as the polymer (E), and as the solvent (D), 3,200 parts by mass of a mixed solvent of (D-1), (D-2), and (D-3), with a mass ratio being 70/29/1; and filtering a resulting mixture through a membrane filter having a pore size of 0.2 μm.

Examples 2 to 46, Comparative Examples 1 to 8, and Reference Examples 1 to 3

Radiation-sensitive resin compositions (J-2) to (J-46) and (CJ-1) to (CJ-11) were prepared in a similar manner to Example 1, except that for each component, the type and content shown in Table 4 below were used.

TABLE 4

| | Radiation-sensitive resin composition | (A) Polymer type | (A) content (parts by mass) | (B) Acid generating agent type | (B) content (parts by mass) | (C) Acid diffusion control agent type | (C) content (parts by mass) | (E) Polymer type | (E) content (parts by mass) | (D) Solvent type | (D) content (parts by mass) |
|---|---|---|---|---|---|---|---|---|---|---|---|
| Example 1 | J-1 | A-1 | 100 | B-5 | 14.0 | C-1 | 2.3 | E-1 | 5.0 | D-1/D-2/D-3 | 3,200 |
| Example 2 | J-2 | A-1 | 100 | B-5 | 14.0 | C-2 | 2.3 | E-1 | 5.0 | D-1/D-2/D-3 | 3,200 |
| Example 3 | J-3 | A-1 | 100 | B-5 | 14.0 | C-3 | 2.3 | E-1 | 5.0 | D-1/D-2/D-3 | 3,200 |
| Example 4 | J-4 | A-1 | 100 | B-5 | 14.0 | C-4 | 2.3 | E-1 | 5.0 | D-1/D-2/D-3 | 3,200 |
| Example 5 | J-5 | A-1 | 100 | B-5 | 14.0 | C-5 | 2.3 | E-1 | 5.0 | D-1/D-2/D-3 | 3,200 |
| Example 6 | J-6 | A-1 | 100 | B-5 | 14.0 | C-6 | 2.3 | E-1 | 5.0 | D-1/D-2/D-3 | 3,200 |
| Example 7 | J-7 | A-1 | 100 | B-5 | 14.0 | C-7 | 2.3 | E-1 | 5.0 | D-1/D-2/D-3 | 3,200 |
| Example 8 | J-8 | A-1 | 100 | B-5 | 14.0 | C-8 | 2.3 | E-1 | 5.0 | D-1/D-2/D-3 | 3,200 |
| Example 9 | J-9 | A-1 | 100 | B-5 | 14.0 | C-9 | 2.3 | E-1 | 5.0 | D-1/D-2/D-3 | 3,200 |
| Example 10 | J-10 | A-1 | 100 | B-5 | 14.0 | C-10 | 2.3 | E-1 | 5.0 | D-1/D-2/D-3 | 3,200 |
| Example 11 | J-11 | A-1 | 100 | B-5 | 14.0 | C-11 | 2.3 | E-1 | 5.0 | D-1/D-2/D-3 | 3,200 |
| Example 12 | J-12 | A-1 | 100 | B-5 | 14.0 | C-12 | 2.3 | E-1 | 5.0 | D-1/D-2/D-3 | 3,200 |
| Example 13 | J-13 | A-1 | 100 | B-5 | 14.0 | C-13 | 2.3 | E-1 | 5.0 | D-1/D-2/D-3 | 3,200 |
| Example 14 | J-14 | A-1 | 100 | B-5 | 14.0 | C-14 | 2.3 | E-1 | 5.0 | D-1/D-2/D-3 | 3,200 |
| Example 15 | J-15 | A-1 | 100 | B-5 | 14.0 | C-15 | 2.3 | E-1 | 5.0 | D-1/D-2/D-3 | 3,200 |
| Example 16 | J-16 | A-1 | 100 | B-5 | 14.0 | C-16 | 2.3 | E-1 | 5.0 | D-1/D-2/D-3 | 3,200 |
| Example 17 | J-17 | A-1 | 100 | B-5 | 14.0 | C-17 | 2.3 | E-1 | 5.0 | D-1/D-2/D-3 | 3,200 |
| Example 18 | J-18 | A-1 | 100 | B-5 | 14.0 | C-18 | 2.3 | E-1 | 5.0 | D-1/D-2/D-3 | 3,200 |
| Example 19 | J-19 | A-2 | 100 | B-5 | 14.0 | C-1 | 2.3 | E-1 | 5.0 | D-1/D-2/D-3 | 3,200 |
| Example 20 | J-20 | A-3 | 100 | B-5 | 14.0 | C-1 | 2.3 | E-1 | 5.0 | D-1/D-2/D-3 | 3,200 |
| Example 21 | J-21 | A-4 | 100 | B-5 | 14.0 | C-1 | 2.3 | E-1 | 5.0 | D-1/D-2/D-3 | 3,200 |
| Example 22 | J-22 | A-5 | 100 | B-5 | 14.0 | C-1 | 2.3 | E-1 | 5.0 | D-1/D-2/D-3 | 3,200 |
| Example 23 | J-23 | A-6 | 100 | B-5 | 14.0 | C-1 | 2.3 | E-1 | 5.0 | D-1/D-2/D-3 | 3,200 |
| Example 24 | J-24 | A-7 | 100 | B-5 | 14.0 | C-1 | 2.3 | E-1 | 5.0 | D-1/D-2/D-3 | 3,200 |
| Example 25 | J-25 | A-8 | 100 | B-5 | 14.0 | C-1 | 2.3 | E-1 | 5.0 | D-1/D-2/D-3 | 3,200 |
| Example 26 | J-26 | A-9 | 100 | B-5 | 14.0 | C-1 | 2.3 | E-1 | 5.0 | D-1/D-2/D-3 | 3,200 |
| Example 27 | J-27 | A-10 | 100 | B-5 | 14.0 | C-1 | 2.3 | E-1 | 5.0 | D-1/D-2/D-3 | 3,200 |
| Example 28 | J-28 | A-11 | 100 | B-5 | 14.0 | C-1 | 2.3 | E-1 | 5.0 | D-1/D-2/D-3 | 3,200 |
| Example 29 | J-29 | A-1 | 100 | B-1 | 14.0 | C-1 | 2.3 | E-1 | 5.0 | D-1/D-2/D-3 | 3,200 |
| Example 30 | J-30 | A-1 | 100 | B-2 | 14.0 | C-1 | 2.3 | E-1 | 5.0 | D-1/D-2/D-3 | 3,200 |
| Example 31 | J-31 | A-1 | 100 | B-3 | 14.0 | C-1 | 2.3 | E-1 | 5.0 | D-1/D-2/D-3 | 3,200 |
| Example 32 | J-32 | A-1 | 100 | B-4 | 14.0 | C-1 | 2.3 | E-1 | 5.0 | D-1/D-2/D-3 | 3,200 |
| Example 33 | J-33 | A-1 | 100 | B-6 | 14.0 | C-1 | 2.3 | E-1 | 5.0 | D-1/D-2/D-3 | 3,200 |
| Example 34 | J-34 | A-1 | 100 | B-7 | 14.0 | C-1 | 2.3 | E-1 | 5.0 | D-1/D-2/D-3 | 3,200 |
| Example 35 | J-35 | A-1 | 100 | B-8 | 14.0 | C-1 | 2.3 | E-1 | 5.0 | D-1/D-2/D-3 | 3,200 |
| Example 36 | J-36 | A-1 | 100 | B-9 | 14.0 | C-1 | 2.3 | E-1 | 5.0 | D-1/D-2/D-3 | 3,200 |
| Example 37 | J-37 | A-1 | 100 | B-10 | 14.0 | C-1 | 2.3 | E-1 | 5.0 | D-1/D-2/D-3 | 3,200 |
| Example 38 | J-38 | A-1 | 100 | B-11 | 14.0 | C-1 | 2.3 | E-1 | 5.0 | D-1/D-2/D-3 | 3,200 |
| Example 39 | J-39 | A-1 | 100 | B-12 | 14.0 | C-1 | 2.3 | E-1 | 5.0 | D-1/D-2/D-3 | 3,200 |
| Example 40 | J-40 | A-1 | 100 | B-13 | 14.0 | C-1 | 2.3 | E-1 | 5.0 | D-1/D-2/D-3 | 3,200 |
| Example 41 | J-41 | A-1 | 100 | B-14 | 14.0 | C-1 | 2.3 | E-1 | 5.0 | D-1/D-2/D-3 | 3,200 |
| Example 42 | J-42 | A-1 | 100 | B-15 | 14.0 | C-1 | 2.3 | E-1 | 5.0 | D-1/D-2/D-3 | 3,200 |
| Example 43 | J-43 | A-1 | 100 | B-16 | 14.0 | C-1 | 2.3 | E-1 | 5.0 | D-1/D-2/D-3 | 3,200 |
| Example 44 | J-44 | A-1 | 100 | B-5 | 14.0 | C-1 | 2.3 | E-2 | 5.0 | D-1/D-2/D-3 | 3,200 |
| Example 45 | J-45 | A-1 | 100 | B-5 | 14.0 | C-1 | 2.3 | E-3 | 5.0 | D-1/D-2/D-3 | 3,200 |
| Example 46 | J-46 | A-1 | 100 | B-5 | 14.0 | C-1 | 2.3 | E-4 | 5.0 | D-1/D-2/D-3 | 3,200 |
| Comparative Example 1 | CJ-1 | A-1 | 100 | B-5 | 14.0 | cc-1 | 2.3 | E-1 | 5.0 | D-1/D-2/13-3 | 3,200 |
| Comparative Example 2 | CJ-2 | A-1 | 100 | B-5 | 14.0 | cc-2 | 2.3 | E-1 | 5.0 | D-1/D-2/13-3 | 3,200 |
| Comparative Example 3 | CJ-3 | A-1 | 100 | B-5 | 14.0 | cc-3 | 2.3 | E-1 | 5.0 | D-1/D-2/13-3 | 3,200 |
| Comparative Example 4 | CJ-4 | A-1 | 100 | B-5 | 14.0 | cc-4 | 2.3 | E-1 | 5.0 | D-1/D-2/13-3 | 3,200 |
| Comparative Example 5 | CJ-5 | A-1 | 100 | B-5 | 14.0 | cc-5 | 2.3 | E-1 | 5.0 | D-1/D-2/13-3 | 3,200 |
| Comparative Example 6 | CJ-6 | A-1 | 100 | B-5 | 14.0 | cc-6 | 2.3 | E-1 | 5.0 | D-1/D-2/D-3 | 3,200 |

TABLE 4-continued

| Radiation-sensitive resin composition | (A) Polymer type | content (parts by mass) | (B) Acid generating agent type | content (parts by mass) | (C) Acid diffusion control agent type | content (parts by mass) | (E) Polymer type | content (parts by mass) | (D) Solvent type | content (parts by mass) |
|---|---|---|---|---|---|---|---|---|---|---|
| Comparative Example 7 | CJ-7 | A-1 | 100 | B-5 | 14.0 | cc-7 | 2.3 | E-1 | 5.0 | D-1/D-2/D-3 | 3,200 |
| Comparative Example 8 | CJ-8 | A-1 | 100 | B-5 | 14.0 | cc-9 | 2.3 | E-1 | 5.0 | D-1/D-2/D-3 | 3,200 |
| Comparative Example 9 | CJ-9 | A-1 | 100 | B-5 | 14.0 | cc-8 | 2.3 | E-1 | 5.0 | D-1/D-2/D-3 | 3,200 |
| Comparative Example 10 | CJ-10 | A-1 | 100 | B-13 | 14.0 | cc-8 | 2.3 | E-1 | 5.0 | D-1/D-2/D-3 | 3,200 |
| Comparative Example 11 | CJ-11 | A-1 | 100 | B-14 | 14.0 | cc-8 | 2.3 | E-1 | 5.0 | D-1/D-2/D-3 | 3,200 |

Resist Pattern Formation Using Negative-Tone Radiation-Sensitive Resin Composition for ArF Exposure An underlayer antireflective film having an average thickness of 105 nm was formed by applying a composition for underlayer antireflective film formation ("ARC66," available from Brewer Science, Inc.) on the surface of a 12-inch silicon wafer using a spin-coater ("CLEAN TRACK ACT12," available from Tokyo Electron Limited), and thereafter baking the composition at 205° C. for 60 sec. Each negative-tone radiation-sensitive resin composition for ArF exposure prepared as described above was applied on the underlayer antireflective film using the spin-coater, and subjected to PB (prebaking) at 90° C. for 60 sec. Thereafter, by cooling at 23° C. for 30 sec, a resist film having an average thickness of 90 nm was formed. Next, the resist pattern was exposed using an ArF excimer laser immersion scanner ("TWINSCAN XT-1900i," available from ASML Co.) through a mask pattern having spaces of 40 nm and pitches of 105 nm at optical conditions involving: NA of 1.35, and Annular ($\sigma$=0.8/0.6). After the exposure, PEB (post-exposure baking) was carried out at 90° C. for 60 sec. Thereafter, the resist film was developed with an organic solvent by using n-butyl acetate as an organic solvent developer solution, followed by drying to form a negative-tone resist pattern (40-nm line-and-space pattern). Furthermore, a negative-tone resist pattern (40 nm holes, 105 nm pitches) was formed by a similar operation, except that the mask pattern was changed.

Evaluations

The resist patterns formed using the radiation-sensitive resin compositions for ArF exposure were evaluated on sensitivity, LWR performance, and CDU performance in accordance with the following methods. The results are shown in Table 5 below. It is to be noted that a scanning electron microscope ("CG-5000," available from Hitachi High-Technologies Corporation) was used for line-width measurement of the resist pattern.

Sensitivity

An exposure dose at which a 40-nm line-and-space pattern was formed in the aforementioned resist pattern formation using the radiation-sensitive resin composition for ArF exposure was defined as an optimum exposure dose, and this optimum exposure dose was adopted as sensitivity (mJ/cm$^2$). The sensitivity was evaluated to be: "favorable" in a case of being no greater than 25 mJ/cm$^2$; and "unfavorable" in a case of exceeding 25 mJ/cm$^2$.

LWR Performance

With a mask size having been adjusted so as to form a 40-nm line and space pattern, irradiation was performed at the optimal exposure dose at which the aforementioned sensitivity was determined, whereby a resist pattern was formed. The resist pattern formed was observed from above by using the scanning electron microscope. Variance of line width was measured at 500 points, and then a 3 Sigma value was determined from distribution of the measurements, and the 3 Sigma value was defined as "LWR performance (nm)." The value being smaller reveals less line roughness, indicating better LWR performance. The LWR performance was evaluated to be: "favorable" in a case of being no greater than 4.5 nm; and "unfavorable" in a case of being greater than 4.5 nm.

CDU Performance

For a resist pattern with holes of 40 nm and pitches of 105 nm, a total of 1,800 line-width measurements were taken from above at arbitrary points by using the scanning electron microscope. Line dimension variation (3$\sigma$) was determined, and this was defined as "CDU performance (nm)." The value being smaller indicates a more favorable CDU performance, revealing less variance of the hole diameters in greater ranges. The CDU performance was evaluated to be: "favorable" in a case of being no greater than 4.8 nm; and "unfavorable" in a case of being greater than 4.8 nm.

TABLE 5

| | Radiation-sensitive resin composition | Sensitivity (mJ/cm$^2$) | CDU (nm) | LWR (nm) |
|---|---|---|---|---|
| Example 1 | J-1 | 19.2 | 4.29 | 4.31 |
| Example 2 | J-2 | 19.7 | 4.52 | 4.12 |
| Example 3 | J-3 | 20.1 | 4.68 | 4.44 |
| Example 4 | J-4 | 19.1 | 4.77 | 4.34 |
| Example 5 | J-5 | 18.2 | 4.44 | 4.29 |
| Example 6 | J-6 | 20.9 | 4.55 | 4.48 |
| Example 7 | J-7 | 21.9 | 4.60 | 4.11 |
| Example 8 | J-8 | 19.3 | 4.63 | 4.41 |
| Example 9 | J-9 | 22.1 | 4.49 | 4.39 |
| Example 10 | J-10 | 18.2 | 4.78 | 4.40 |
| Example 11 | J-11 | 17.2 | 4.72 | 4.09 |
| Example 12 | J-12 | 17.9 | 4.33 | 4.20 |
| Example 13 | J-13 | 18.1 | 4.47 | 4.42 |
| Example 14 | J-14 | 21.1 | 4.53 | 4.38 |
| Example 15 | J-15 | 23.0 | 4.64 | 4.42 |
| Example 16 | J-16 | 21.0 | 4.33 | 4.22 |
| Example 17 | J-17 | 19.3 | 4.50 | 4.41 |
| Example 18 | J-18 | 18.2 | 4.30 | 4.45 |
| Example 19 | J-19 | 21.0 | 4.34 | 4.15 |
| Example 20 | J-20 | 22.9 | 4.42 | 4.25 |
| Example 21 | J-21 | 23.1 | 4.49 | 4.04 |
| Example 22 | J-22 | 21.2 | 4.41 | 4.01 |
| Example 23 | J-23 | 20.4 | 4.22 | 4.15 |
| Example 24 | J-24 | 19.8 | 4.21 | 3.93 |
| Example 25 | J-25 | 20.8 | 4.14 | 4.11 |
| Example 26 | J-26 | 23.3 | 4.51 | 4.19 |
| Example 27 | J-27 | 21.5 | 4.35 | 4.29 |

TABLE 5-continued

|  | Radiation-sensitive resin composition | Sensitivity (mJ/cm²) | CDU (nm) | LWR (nm) |
|---|---|---|---|---|
| Example 28 | J-28 | 19.9 | 4.41 | 4.21 |
| Example 29 | J-29 | 19.5 | 4.70 | 4.35 |
| Example 30 | J-30 | 20.7 | 4.77 | 4.04 |
| Example 31 | J-31 | 23.7 | 4.48 | 4.15 |
| Example 32 | J-32 | 22.9 | 4.53 | 4.37 |
| Example 33 | J-33 | 23.0 | 4.56 | 4.33 |
| Example 34 | J-34 | 21.9 | 4.42 | 4.37 |
| Example 35 | J-35 | 24.3 | 4.71 | 4.17 |
| Example 36 | J-36 | 24.2 | 4.22 | 4.36 |
| Example 37 | J-37 | 23.9 | 4.45 | 4.40 |
| Example 38 | J-38 | 22.2 | 4.61 | 4.39 |
| Example 39 | J-39 | 21.4 | 4.70 | 4.33 |
| Example 40 | J-40 | 24.4 | 4.57 | 4.40 |
| Example 41 | J-41 | 23.8 | 4.55 | 4.38 |
| Example 42 | J-42 | 23.9 | 4.67 | 4.33 |
| Example 43 | J-43 | 21.2 | 4.48 | 4.45 |
| Example 44 | J-44 | 19.2 | 4.30 | 4.33 |
| Example 45 | J-45 | 19.1 | 4.25 | 4.33 |
| Example 46 | J-46 | 19.6 | 4.22 | 4.39 |
| Comparative Example 1 | CJ-1 | 28.7 | 5.23 | 5.22 |
| Comparative Example 2 | CJ-2 | 26.5 | 5.12 | 5.72 |
| Comparative Example 3 | CJ-3 | 26.9 | 5.21 | 5.23 |
| Comparative Example 4 | CJ-4 | 27.2 | 4.91 | 5.85 |
| Comparative Example 5 | CJ-5 | 32.8 | 5.52 | 5.78 |
| Comparative Example 6 | CJ-6 | 25.1 | 4.91 | 5.11 |
| Comparative Example 7 | CJ-7 | 23.9 | 4.99 | 5.19 |
| Comparative Example 8 | CJ-8 | 24.8 | 4.88 | 5.02 |
| Comparative Example 9 | CJ-9 | 26.8 | 5.11 | 4.99 |
| Comparative Example 10 | CJ-10 | 27.9 | 5.01 | 5.03 |
| Comparative Example 11 | CJ-11 | 25.9 | 4.96 | 4.96 |

As is clear from the results shown in Table 5, in the case of use for ArF exposure, the radiation-sensitive resin compositions of the Examples were favorable in terms of the sensitivity, the LWR performance, and the CDU performance, while the Comparative Examples and the Reference Examples were inferior in terms of each characteristic when compared to the Examples. Accordingly, using the radiation-sensitive resin compositions of the Examples for ArF exposure enables formation of a resist pattern having high sensitivity, as well as superiority in the LWR performance and the CDU performance.

Preparation of Radiation-Sensitive Resin Composition for Ultraviolet Ray (EUV) Exposure Example 47

A radiation-sensitive resin composition (J-47) was prepared by: mixing 100 parts by mass of (A-12) as the polymer (A), 20.0 parts by mass of (B-4) as the acid generating agent (B), 3.2 parts by mass of (C-1) as the acid diffusion control agent (C), 3.0 parts by mass of (E-5) as the polymer (E), and as the solvent (D), 6,000 parts by mass of a mixed solvent of (D-1) and (D-4), with a mass ratio being 70/30; and filtering a resulting mixture through a membrane filter having a pore size of 0.2 μm.

Examples 48 to 58 and Comparative Examples 9 to 12

Radiation-sensitive resin compositions (J-48) to (J-58) and (CJ-12) to (CJ-15) were prepared in a similar manner to Example 47, except that for each component, the type and content shown in Table 6 below were used.

TABLE 6

| | Radiation-sensitive resin composition | (A) Polymer | | (B) Acid generating agent | | (C) Acid diffusion control agent | | (E) Polymer | | (D) Organic solvent | |
|---|---|---|---|---|---|---|---|---|---|---|---|
| | | Type | content (parts by mass) | type | content (parts by mass) | type | content (parts by mass) | type | content (parts by mass) | type | content (parts by mass) |
| Example 47 | J-47 | A-12 | 100 | B-4 | 20.0 | C-1 | 3.2 | E-5 | 3.0 | D-1/D-4 | 6,000 |
| Example 48 | J-48 | A-12 | 100 | B-4 | 20.0 | C-2 | 3.2 | E-5 | 3.0 | D-1/D-4 | 6,000 |
| Example 49 | J-49 | A-12 | 100 | B-4 | 20.0 | C-5 | 3.2 | E-5 | 3.0 | D-1/D-4 | 6,000 |
| Example 50 | J-50 | A-12 | 100 | B-4 | 20.0 | C-11 | 3.2 | E-5 | 3.0 | D-1/D-4 | 6,000 |
| Example 51 | J-51 | A-12 | 100 | B-4 | 20.0 | C-17 | 3.2 | E-5 | 3.0 | D-1/D-4 | 6,000 |
| Example 52 | J-52 | A-13 | 100 | B-4 | 20.0 | C-1 | 3.2 | E-5 | 3.0 | D-1/D-4 | 6,000 |
| Example 53 | J-53 | A-14 | 100 | B-4 | 20.0 | C-1 | 3.2 | E-5 | 3.0 | D-1/D-4 | 6,000 |
| Example 54 | J-54 | A-15 | 100 | B-4 | 20.0 | C-1 | 3.2 | E-5 | 3.0 | D-1/D-4 | 6,000 |
| Example 55 | J-55 | A-12 | 100 | B-5 | 20.0 | C-1 | 3.2 | E-5 | 3.0 | D-1/D-4 | 6,000 |
| Example 56 | J-56 | A-12 | 100 | B-11 | 20.0 | C-1 | 3.2 | E-5 | 3.0 | D-1/D-4 | 6,000 |
| Example 57 | J-57 | A-12 | 100 | B-13 | 20.0 | C-1 | 3.2 | E-5 | 3.0 | D-1/D-4 | 6,000 |
| Example 58 | J-58 | A-12 | 100 | B-14 | 20.0 | C-1 | 3.2 | E-5 | 3.0 | D-1/D-4 | 6,000 |
| Comparative Example 12 | CJ-12 | A-12 | 100 | B-4 | 20.0 | cc-1 | 3.2 | E-5 | 3.0 | D-1/D-4 | 6,000 |
| Comparative Example 13 | CJ-13 | A-12 | 100 | B-4 | 20.0 | cc-2 | 3.2 | E-5 | 3.0 | D-1/D-4 | 6,000 |
| Comparative Example 14 | CJ-14 | A-12 | 100 | B-4 | 20.0 | cc-6 | 3.2 | E-5 | 3.0 | D-1/D-4 | 6,000 |
| Comparative Example 15 | CJ-15 | A-12 | 100 | B-4 | 20.0 | cc-9 | 3.2 | E-5 | 3.0 | D-1/D-4 | 6,000 |

Resist Pattern Formation Using Radiation-Sensitive Resin Composition for EUV Exposure An underlayer antireflective film having an average thickness of 105 nm was formed by applying a composition for underlayer antireflective film formation ("ARC66," available from Brewer Science, Inc.) on the surface of a 12-inch silicon wafer using a spin-coater ("CLEAN TRACK ACT12," available from Tokyo Electron Limited), and thereafter baking the composition at 205° C. for 60 sec. Each radiation-sensitive resin composition for EUV exposure prepared as described above was applied on the underlayer antireflective film using the spin-coater, and subjected to PB at 130° C. for 60 sec. Thereafter, by cooling at 23° C. for 30 sec, a resist film having an average thickness of 55 nm was formed. Next, the resist film was exposed using an EUV scanner ("NXE3300", available from ASML Co.) with NA of 0.33 under an illumination condition of Conventional s=0.89 and with a mask of imecDEFECT32FFR02. After the exposure, PEB was carried out at 120° C. for 60 sec. Thereafter, the resist film was developed with an alkali by using a 2.38% by mass aqueous TMAH solution as an alkaline developer solution, followed by washing with water and further drying to form a positive-tone resist pattern (32-nm line-and-space pattern).

Evaluations

The resist patterns formed using the radiation-sensitive resin compositions for EUV exposure were evaluated on sensitivity and LWR performance in accordance with the following methods. The results are shown in Table 7 below. It is to be noted that a scanning electron microscope ("CG-5000," available from Hitachi High-Technologies Corporation) was used for line-width measurement of the resist pattern.

Sensitivity

An exposure dose at which a 32-nm line-and-space pattern was formed in the aforementioned resist pattern formation using the radiation-sensitive resin composition for EUV exposure was defined as an optimum exposure dose, and this optimum exposure dose was adopted as sensitivity (mJ/cm$^2$). The sensitivity was evaluated to be: "favorable" in a case of being no greater than 34 mJ/cm$^2$; and "unfavorable" in a case of exceeding 34 mJ/cm$^2$.

LWR Performance

With a mask size having been adjusted so as to form a 32-nm line and space pattern, irradiation was performed at the optimal exposure dose at which the aforementioned sensitivity was determined, whereby a resist pattern was formed. The resist pattern formed was observed from above using the aforementioned scanning electron microscope. Variance of line width was measured at 500 points, and then a 3 Sigma value was determined from distribution of the measurements, and the 3 Sigma value was defined as "LWR performance (nm)." The value being smaller reveals less line rattling, indicating better LWR performance. The LWR performance was evaluated to be: "favorable" in a case of being no greater than 3.6 nm; and "unfavorable" in a case of being greater than 3.6 nm.

TABLE 7

| | Radiation-sensitive resin composition | Sensitivity (mJ/cm$^2$) | LWR (nm) |
|---|---|---|---|
| Example 47 | J-47 | 32.9 | 3.22 |
| Example 48 | J-48 | 32.3 | 3.19 |
| Example 49 | J-49 | 31.7 | 3.33 |
| Example 50 | J-50 | 31.1 | 3.26 |
| Example 51 | J-51 | 32.9 | 3.31 |
| Example 52 | J-52 | 31.1 | 3.42 |
| Example 53 | J-53 | 32.1 | 3.29 |
| Example 54 | J-54 | 33.7 | 3.44 |
| Example 55 | J-55 | 31.3 | 3.55 |
| Example 56 | J-56 | 33.2 | 3.24 |
| Example 57 | J-57 | 32.4 | 3.43 |
| Example 58 | J-58 | 32.6 | 3.46 |
| Comparative Example 12 | CJ-12 | 42.1 | 3.98 |
| Comparative Example 13 | CJ-13 | 41.2 | 4.09 |
| Comparative Example 14 | CJ-14 | 39.9 | 4.22 |
| Comparative Example 15 | CJ-15 | 38.8 | 4.18 |

As is clear from the results shown in Table 7, in the case of use for EUV exposure, the radiation-sensitive resin compositions of the Examples were favorable in terms of the sensitivity and the LWR performance, while the Comparative Examples were inferior in terms of each characteristic when compared to the Examples.

Preparation of Positive-Tone Radiation-Sensitive Resin Compositions for ArF Exposure, and Formation and Evaluations of Resist Patterns Using the Compositions

Example 59

A radiation-sensitive resin composition (J-59) was prepared by: mixing 100 parts by mass of (A-4) as the polymer (A), 14.0 parts by mass of (B-5) as the acid generating agent (B), 2.3 parts by mass of (C-1) as the acid diffusion control agent (C), 5.0 parts by mass (solid content) of (E-2) as the polymer (E), and as the solvent (D), 3,200 parts by mass of a mixed solvent of (D-1), (D-2), and (D-3), with a mass ratio being 70/29/1; and filtering a resulting mixture through a membrane filter having a pore size of 0.2 μm.

An underlayer antireflective film having an average thickness of 105 nm was formed by applying a composition for underlayer antireflective film formation ("ARC66," available from Brewer Science, Inc.) on the surface of a 12-inch silicon wafer using a spin-coater ("CLEAN TRACK ACT12," available from Tokyo Electron Limited), and thereafter baking the composition at 205° C. for 60 sec. Each positive-tone radiation-sensitive resin composition for ArF exposure (J-59) prepared as described above was applied on the underlayer antireflective film using the spin-coater, and subjected to PB (prebaking) at 90° C. for 60 sec. Thereafter, by cooling at 23° C. for 30 sec, a resist film having an average thickness of 90 nm was formed. Next, the resist pattern was exposed using an ArF excimer laser immersion scanner ("TWINSCAN XT-1900i," available from ASML Co.) through a mask pattern having spaces of 40 nm and pitches of 105 nm at optical conditions involving: NA of 1.35, and Annular (σ=0.8/0.6). After the exposure, PEB (post-exposure baking) was carried out at 90° C. for 60 sec. Thereafter, the resist film was developed with an alkali by using a 2.38% by mass aqueous TMAH solution as an alkaline developer solution, followed by washing with water and further drying to form a positive-tone resist pattern (40-nm line-and-space pattern).

The resist pattern formed using the positive-tone radiation-sensitive resin composition for ArF exposure was given evaluations similar to the evaluations of the resist pattern formed using the negative-tone radiation-sensitive resin composition for ArF exposure. The results of the evaluations revealed that, also in the case of forming the positive-tone resin pattern with ArF exposure, the sensitivity, the LWR performance, and the CDU performance were favorable.

The radiation-sensitive resin composition and the resist pattern-forming method of the embodiments of the present invention enable a resist pattern to be formed with favorable sensitivity to exposure light, and superiority with regard to each of LWR performance and CDU performance. The acid diffusion control agent of the embodiment of the present invention can be suitably used as a component of the radiation-sensitive resin composition. Therefore, these can be suitably used in manufacturing processes of semiconductor devices, in which further progress of miniaturization is expected in the future.

Obviously, numerous modifications and variations of the present invention are possible in light of the above teachings. It is therefore to be understood that within the scope of the appended claims, the invention may be practiced otherwise than as specifically described herein.

What is claimed is:
1. A radiation-sensitive resin composition comprising:
a polymer comprising a structural unit comprising an acid-labile group; and
a compound represented by formula (1):

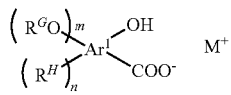

(1)

wherein, in the formula (1),
$Ar^1$ represents a group obtained by removing (m+n+2) hydrogen atoms from an aromatic ring of an arene having 6 to 30 carbon atoms;
—OH and —COO— are bonded at ortho positions to each other on a same benzene ring on $Ar^1$;
m is an integer of 1 to 16, wherein
in a case in which m is 1, $R^G$ represents a group represented by formula (V-1), a group represented by formula (V-2), a group comprising a lactone structure, a group comprising a cyclic carbonate structure, a group comprising a sultone structure, a group comprising a ketonic carbonyl group, a group comprising a thiocarbonate group, or a group comprising a group represented by formula (V-3), and
in a case in which m is no less than 2, a plurality of $R^G$s are identical or different from each other, and each $R^G$ represents a group represented by the formula (V-1), a group represented by the formula (V-2), a group comprising a lactone structure, a group comprising a cyclic carbonate structure, a group comprising a sultone structure, a group comprising a ketonic carbonyl group, a group comprising a thiocarbonate group, or a group comprising a group represented by the formula (V-3), or the plurality of $R^G$s taken together represent a part of a ring structure having 5 to 20 ring atoms constituted together with the atomic chain to which the plurality of $R^G$s bond;
n is an integer of 0 to 15, wherein
in a case in which n is 1, $R^H$ represents a halogen atom or a substituted or unsubstituted monovalent hydrocarbon group having 1 to 20 carbon atoms, and
in a case in which n is no less than 2, a plurality of $R^H$s are identical or different from each other, and each $R^H$ represents a halogen atom or a substituted or unsubstituted monovalent hydrocarbon group having 1 to 20 carbon atoms, or the plurality of $R^H$s taken together represent a part of an alicyclic structure having 4 to 20 ring atoms constituted together with the carbon chain to which the plurality of $R^H$s bond, and wherein
a sum of m and n is no greater than 16; and
$M^+$ is a monovalent radiation-sensitive cation,

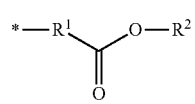

(V-1)

in the formula (V-1),
$R^1$ represents a substituted or unsubstituted divalent hydrocarbon group having 1 to 20 carbon atoms;
$R^2$ represents a monovalent organic group having 1 to 20 carbon atoms; and
* denotes a binding site to an oxygen atom adjacent to $Ar^1$ in the formula (1),

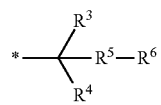

(V-2)

in the formula (V-2),
$R^3$ and $R^4$ each independently represent a hydrogen atom or a substituted or unsubstituted monovalent hydrocarbon group having 1 to 20 carbon atoms;
$R^5$ represents —O— or —S—; and
$R^6$ represents a monovalent organic group having 1 to 20 carbon atoms, or
$R^4$, $R^5$, and $R^6$ taken together represent a part of a ring structure having 4 to 20 ring atoms constituted together with the atomic chain to which $R^4$, $R^5$, and $R^6$ bond; and
* denotes a binding site to an oxygen atom adjacent to $Ar^1$ in the formula (1), and

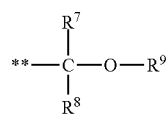

(V-3)

in the formula (V-3),
$R^7$ represents a fluorine atom or a monovalent fluorinated hydrocarbon group having 1 to 20 carbon atoms;
$R^8$ represents a hydrogen atom, a fluorine atom, or a monovalent organic group having 1 to 20 carbon atoms;
$R^9$ represents a hydrogen atom or a monovalent organic group having 1 to 20 carbon atoms; and
** denotes a binding site to an oxygen atom adjacent to $Ar^1$ in the formula (1) or to a part other than the group represented by the formula (V-3) in $R^G$.

2. The radiation-sensitive resin composition according to claim 1, further comprising an acid generator which is capable of generating an acid by irradiation with a radioactive ray.

3. The radiation-sensitive resin composition according to claim 1, wherein $R^2$ in the formula (V-1), $R^6$ in the formula (V-2), and $R^9$ in the formula (V-3) each independently represent a monovalent hydrocarbon group having 1 to 20 carbon atoms in which a part or all of hydrogen atoms are optionally substituted with a hetero atom-containing group; or a monovalent group that includes a divalent hetero atom-containing group between two adjacent carbon atoms of or at an end of the monovalent hydrocarbon group in which a part or all of hydrogen atoms are optionally substituted with a hetero atom-containing group.

4. The radiation-sensitive resin composition according to claim 1, wherein $R^G$ in the formula (1) represents a group comprising a lactone structure, a group comprising a cyclic carbonate structure, or a group comprising a sultone structure.

5. The radiation-sensitive resin composition according to claim 1, wherein $R^G$ in the formula (1) represents a group represented by the formula (V-1).

6. The radiation-sensitive resin composition according to claim 5, wherein $R^2$ in the formula (V-1) represents a monovalent organic group having 1 to 20 carbon atoms and having a ring structure with 3 to 12 ring atoms.

7. The radiation-sensitive resin composition according to claim 1, wherein m in the formula (1) is 2, and two $R^G$s each independently represent a group represented by the formula (V-1).

8. A resist pattern-forming method comprising:
applying a radiation-sensitive resin composition directly or indirectly on a substrate to form a resist film;
exposing the resist film; and
developing the resist film exposed, wherein
the radiation-sensitive resin composition comprises:
a polymer comprising a structural unit comprising an acid-labile group; and
a compound represented by formula (1):

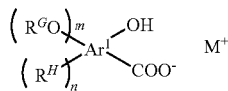

(1)

wherein, in the formula (1),
$Ar^1$ represents a group obtained by removing (m+n+2) hydrogen atoms from an aromatic ring of an arene having 6 to 30 carbon atoms;
—OH and —COO— are bonded at ortho positions to each other on a same benzene ring on $Ar^1$;
m is an integer of 1 to 16, wherein
in a case in which m is 1, $R^G$ represents a group represented by formula (V-1), a group represented by formula (V-2), a group comprising a lactone structure, a group comprising a cyclic carbonate structure, a group comprising a sultone structure, a group comprising a ketonic carbonyl group, a group comprising a thiocarbonate group, or a group comprising a group represented by the formula (V-3), and
in a case in which m is no less than 2, a plurality of $R^G$s are identical or different from each other, and each $R^G$ represents a group represented by the formula (V-1), a group represented by the formula (V-2), a group comprising a lactone structure, a group comprising a cyclic carbonate structure, a group comprising a sultone structure, a group comprising a ketonic carbonyl group, a group comprising a thiocarbonate group, or a group comprising a group represented by the formula (V-3), or the plurality of $R^G$s taken together represent a part of a ring structure having 5 to 20 ring atoms constituted together with the atomic chain to which the plurality of $R^G$s bond;
n is an integer of 0 to 15, wherein
in a case in which n is 1, $R^H$ represents a halogen atom or a substituted or unsubstituted monovalent hydrocarbon group having 1 to 20 carbon atoms, and
in a case in which n is no less than 2, a plurality of $R^H$s are identical or different from each other, and each $R^H$ represents a halogen atom or a substituted or unsubstituted monovalent hydrocarbon group having 1 to 20 carbon atoms, or the plurality of $R^H$s taken together represent a part of an alicyclic structure having 4 to 20 ring atoms constituted together with the carbon chain to which the plurality of $R^H$s bond, and wherein
a sum of m and n is no greater than 16; and
$M^+$ is a monovalent radiation-sensitive cation,

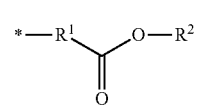

(V-1)

in the formula (V-1),
$R^1$ represents a substituted or unsubstituted divalent hydrocarbon group having 1 to 20 carbon atoms;
$R^2$ represents a monovalent organic group having 1 to 20 carbon atoms; and
* denotes a binding site to an oxygen atom adjacent to $Ar^1$ in the formula (1),

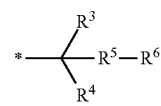

(V-2)

in the formula (V-2),
$R^3$ and $R^4$ each independently represent a hydrogen atom or a substituted or unsubstituted monovalent hydrocarbon group having 1 to 20 carbon atoms;
$R^5$ represents —O— or —S—; and
$R^6$ represents a monovalent organic group having 1 to 20 carbon atoms, or
$R^4$, $R^5$, and $R^6$ taken together represent a part of a ring structure having 4 to 20 ring atoms constituted together with the atomic chain to which $R^4$, $R^5$, and $R^6$ bond; and
* denotes a binding site to an oxygen atom adjacent to $Ar^1$ in the formula (1), and

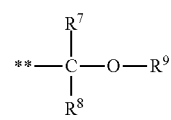

(V-3)

in the formula (V-3), $R^7$ represents a fluorine atom or a monovalent fluorinated hydrocarbon group having 1 to 20 carbon atoms;

$R^8$ represents a hydrogen atom, a fluorine atom, or a monovalent organic group having 1 to 20 carbon atoms;

$R^9$ represents a hydrogen atom or a monovalent organic group having 1 to 20 carbon atoms; and

** denotes a binding site to an oxygen atom adjacent to $Ar^1$ in the formula (1) or to a part other than the group represented by the formula (V-3) in $R^G$.

9. A compound represented by formula (1):

$$\left(R^G O\right)_m \underset{\left(R^H\right)_n}{Ar^1} \underset{COO^-}{OH} \quad M^+ \tag{1}$$

wherein, in the formula (1), $Ar^1$ represents a group obtained by removing (m+n+2) hydrogen atoms from an aromatic ring of an arene having 6 to 30 carbon atoms;

—OH and —COO— are bonded at ortho positions to each other on a same benzene ring on $Ar^1$;

m is an integer of 1 to 16, wherein in a case in which m is 1, $R^G$ represents a group represented by formula (V-1), a group represented by formula (V-2), a group comprising a lactone structure, a group comprising a cyclic carbonate structure, a group comprising a sultone structure, a group comprising a ketonic carbonyl group, a group comprising a thiocarbonate group, or a group comprising a group represented by formula (V-3), and in a case in which m is no less than 2, a plurality of $R^G$s are identical or different from each other, and each $R^G$ represents a group represented by the formula (V-1), a group represented by the formula (V-2), a group comprising a lactone structure, a group comprising a cyclic carbonate structure, a group comprising a sultone structure, a group comprising a ketonic carbonyl group, a group comprising a thiocarbonate group, or a group comprising a group represented by the formula (V-3), or the plurality of $R^G$s taken together represent a part of a ring structure having 5 to 20 ring atoms constituted together with the atomic chain to which the plurality of $R^G$s bond;

n is an integer of 0 to 15, wherein in a case in which n is 1, $R^H$ represents a halogen atom or a substituted or unsubstituted monovalent hydrocarbon group having 1 to 20 carbon atoms, and in a case in which n is no less than 2, a plurality of $R^H$s are identical or different from each other, and each $R^H$ represents a halogen atom or a substituted or unsubstituted monovalent hydrocarbon group having 1 to 20 carbon atoms, or the plurality of $R^H$s taken together represent a part of an alicyclic structure having 4 to 20 ring atoms constituted together with the carbon chain to which the plurality of $R^H$s bond, and wherein a sum of m and n is no greater than 16; and $M^+$ is a monovalent radiation-sensitive cation, $$*-R^1\underset{O}{\overset{}{\diagdown}}O-R^2 \tag{V-1}$$

in the formula (V-1), $R^1$ represents a substituted or unsubstituted divalent hydrocarbon group having 1 to 20 carbon atoms;

$R^2$ represents a monovalent organic group having 1 to 20 carbon atoms; and

* denotes a binding site to an oxygen atom adjacent to $Ar^1$ in the formula (1), $$*-\underset{R^4}{\overset{R^3}{\diagup}}R^5-R^6 \tag{V-2}$$

in the formula (V-2), $R^3$ and $R^4$ each independently represent a hydrogen atom or a substituted or unsubstituted monovalent hydrocarbon group having 1 to 20 carbon atoms;

$R^5$ represents —O— or —S—; and $R^6$ represents a monovalent organic group having 1 to 20 carbon atoms, or $R^4$, $R^5$, and $R^6$ taken together represent a part of a ring structure having 4 to 20 ring atoms constituted together with the atomic chain to which $R^4$, $R^5$, and $R^6$ bond; and

* denotes a binding site to an oxygen atom adjacent to $Ar^1$ in the formula (1), and $$**-\underset{R^8}{\overset{R^7}{\underset{|}{C}}}-O-R^9 \tag{V-3}$$

in the formula (V-3), $R^7$ represents a fluorine atom or a monovalent fluorinated hydrocarbon group having 1 to 20 carbon atoms;

$R^8$ represents a hydrogen atom, a fluorine atom, or a monovalent organic group having 1 to 20 carbon atoms;

$R^9$ represents a hydrogen atom or a monovalent organic group having 1 to 20 carbon atoms; and

** denotes a binding site to an oxygen atom adjacent to $Ar^1$ in the formula (1) or to a part other than the group represented by the formula (V-3) in $R^G$.

10. A method of controlling acid diffusion, comprising:
irradiating a composition which comprises the compound according to claim 9 and an acid generator with a radioactive ray, the acid generator being capable of generating an acid by irradiation with the radioactive ray.

* * * * *